(12) United States Patent
Levine

(10) Patent No.: US 10,828,407 B2
(45) Date of Patent: Nov. 10, 2020

(54) BREAST PUMP KIT

(71) Applicant: Momgenuity, LLC, Bradenton, FL (US)

(72) Inventor: Sherri Levine, Bradenton, FL (US)

( * ) Notice: Subject to any disclaimer, the term of this patent is extended or adjusted under 35 U.S.C. 154(b) by 338 days.

(21) Appl. No.: 15/882,280

(22) Filed: Jan. 29, 2018

(65) Prior Publication Data

US 2019/0175801 A1    Jun. 13, 2019

Related U.S. Application Data

(63) Continuation-in-part of application No. 15/230,869, filed on Aug. 8, 2016, now abandoned, and a continuation-in-part of application No. 14/919,649, filed on Oct. 21, 2015, now Pat. No. 9,878,078, said application No. 15/230,869 is a continuation of
(Continued)

(51) Int. Cl.
*A61M 1/06* (2006.01)
*A61J 9/00* (2006.01)

(52) U.S. Cl.
CPC ............ *A61M 1/064* (2014.02); *A61M 1/062* (2014.02); *A61J 9/00* (2013.01); *A61M 2205/0205* (2013.01); *A61M 2205/07* (2013.01); *A61M 2210/1007* (2013.01)

(58) Field of Classification Search
CPC ........ A61M 1/006; A61M 1/062; A61M 1/06; A61M 2210/1007; A61M 2205/07; A61M 2205/0205; A61M 1/066; A61J 13/00; A61J 9/00; A61J 9/08
See application file for complete search history.

(56) References Cited

U.S. PATENT DOCUMENTS

| 4,642,092 A | 2/1987 | Moss |
| 4,794,915 A | 1/1989 | Larsson |
| 4,799,922 A | 1/1989 | Beer et al. |

(Continued)

FOREIGN PATENT DOCUMENTS

| WO | WO2002087490 | 11/2002 |
| WO | WO 2003/068291 | 8/2003 |

(Continued)

OTHER PUBLICATIONS

U.S. Office Action dated Apr. 13, 2015 in U.S. Appl. No. 14/311,848.
(Continued)

*Primary Examiner* — Jenna Zhang
(74) *Attorney, Agent, or Firm* — Hartman & Citrin LLC

(57) ABSTRACT

Embodiments of a breast pump kit are disclosed herein. The breast pump kit can include one or more of a breast pump shield and a breast pump milk bag. According to various embodiments, the breast pump shield can include a body portion that has a breast engagement portion that can receive at least a portion of a breast of a user. The breast pump shield also can include a suction chamber located in proximity to the breast engagement portion. Milk can pass into the suction chamber and into the breast pump milk bag. A one-way valve can prevent reverse flow of fluids from the breast pump milk bag into the breast pump shield. The breast pump kit also can include a cover that can seal the breast pump shield, if desired.

20 Claims, 18 Drawing Sheets

Related U.S. Application Data application No. 14/311,848, filed on Jun. 23, 2014, now Pat. No. 9,408,957.

(60) Provisional application No. 62/623,141, filed on Jan. 29, 2018.

(56) References Cited

U.S. PATENT DOCUMENTS

| | | | |
|---|---|---|---|
| 5,011,381 | A | 4/1991 | Newa Rd |
| 5,897,580 | A | 4/1999 | Silver |
| 5,941,847 | A | 8/1999 | Huber |
| 6,387,072 | B1 | 5/2002 | Larsson et al. |
| 6,423,030 | B1 | 7/2002 | Silver |
| 6,723,066 | B2 | 4/2004 | Larsson et al. |
| 7,044,828 | B2 | 5/2006 | Foley |
| 7,776,008 | B2 | 8/2010 | Renz et al. |
| 8,187,219 | B1 | 5/2012 | Chiang |
| 8,357,116 | B2 | 1/2013 | Simdon |
| 8,529,501 | B2 | 9/2013 | Wach et al. |
| 9,878,078 | B1 | 1/2018 | Levine |
| 2002/0062103 | A1 | 5/2002 | Larsson et al. |
| 2002/0072702 | A1 | 6/2002 | Quay |
| 2003/0073951 | A1* | 4/2003 | Morton .............. A61B 10/0041 604/73 |
| 2004/0029486 | A1 | 2/2004 | Greter |
| 2004/0074859 | A1 | 4/2004 | Hanna |
| 2004/0122356 | A1 | 6/2004 | Burke et al. |
| 2005/0172577 | A1 | 8/2005 | Oltrogge |
| 2006/0025718 | A1 | 2/2006 | Ostrowski |
| 2007/0173756 | A1 | 7/2007 | Krebs |
| 2008/0208115 | A1* | 8/2008 | Kliegman ........... A61M 1/0068 604/74 |
| 2009/0062731 | A1* | 3/2009 | Keyong ................. A61M 1/06 604/74 |
| 2011/0251552 | A1 | 10/2011 | Brittner |
| 2011/0301532 | A1* | 12/2011 | Wach .................... A61M 1/062 604/74 |
| 2012/0041365 | A1* | 2/2012 | Simdon ................. A61M 1/06 604/74 |
| 2012/0065608 | A1 | 3/2012 | Costello et al. |
| 2014/0236072 | A1* | 8/2014 | Zhang .................. A61M 35/00 604/23 |
| 2014/0305817 | A1* | 10/2014 | Guery ............... B65D 51/2892 206/221 |
| 2015/0024658 | A1 | 1/2015 | Abbott |
| 2016/0287766 | A1* | 10/2016 | Bambino .............. A61M 1/062 |

FOREIGN PATENT DOCUMENTS

| | | |
|---|---|---|
| WO | WO2012021252 | 2/2012 |
| WO | WO 2013/088310 | 6/2013 |
| WO | WO 2013/066919 | 10/2013 |

OTHER PUBLICATIONS

U.S. Office Action dated Dec. 11, 2015 in U.S. Appl. No. 14/311,848.
U.S. Notice of Allowance dated Mar. 25, 2016 in U.S. Appl. No. 14/311,848.
U.S. Office Action dated Apr. 11, 2017 in U.S. Appl. No. 15/230,869.
U.S. Office Action dated Nov. 7, 2017 in U.S. Appl. No. 15/230,869.
U.S. Office Action dated Mar. 8, 2017 in U.S. Appl. No. 14/919,649.
U.S. Notice of Allowance dated Sep. 5, 2017 in U.S. Appl. No. 14/919,649.
InternationalSearch Report and Written Opinion dated May 14, 2019 in International Application No. PCT/US2019/015403.

* cited by examiner

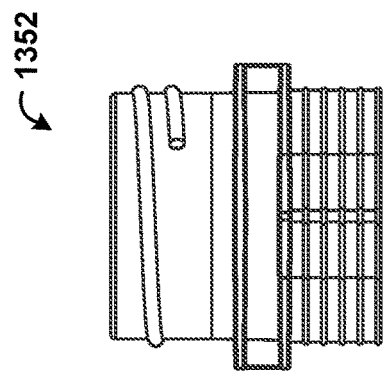
FIG. 23
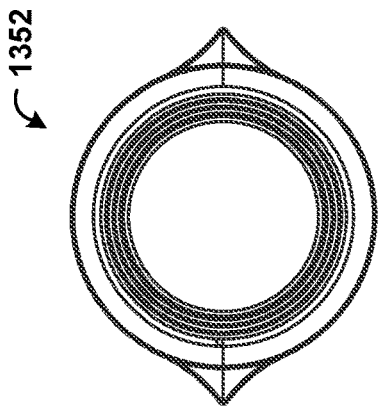
FIG. 25
FIG. 22
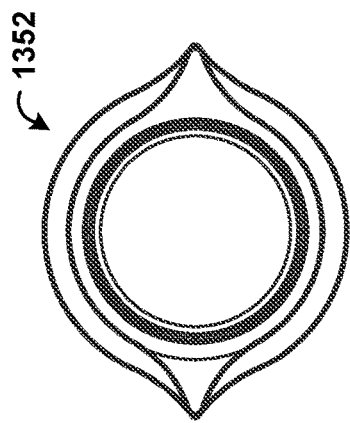
FIG. 24
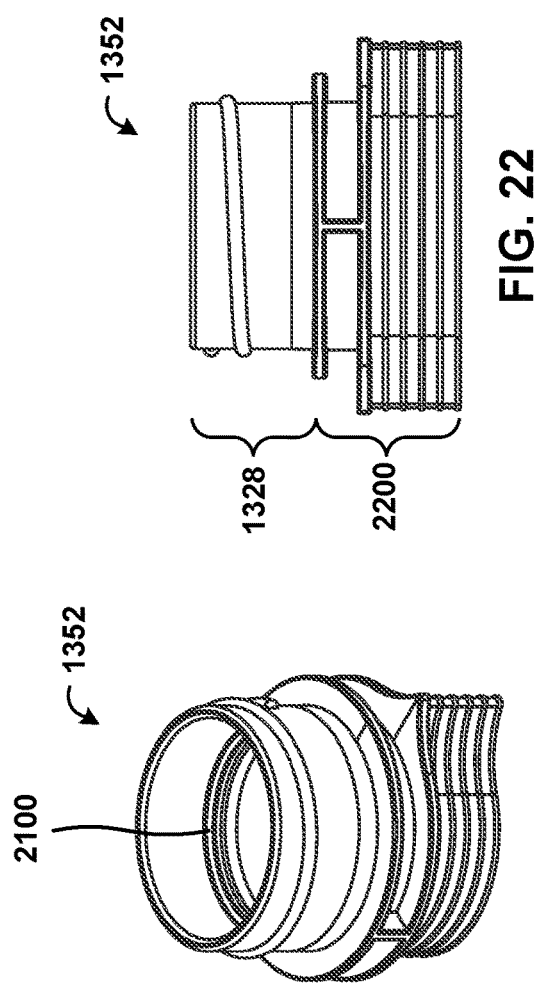
FIG. 21

BREAST PUMP KIT

CROSS-REFERENCE TO RELATED APPLICATIONS

This application is a non-provisional of and claims priority to U.S. Prov. Pat. App. No. 62/623,141, entitled "Disposable Breast Pump Kit," filed Jan. 29, 2018, which is incorporated herein by reference in its entirety. This application also is a continuation-in-part of and claims priority to U.S. patent application Ser. No. 14/919,649, entitled "Disposable Breast Pump Shield," filed Oct. 21, 2015, now U.S. Pat. No. 9,878,078, which is incorporated herein by reference in its entirety. This application also is a continuation-in-part of and claims priority to U.S. patent application Ser. No. 15/230,869, entitled "Breast Pump Shield," filed Aug. 8, 2016, which is incorporated herein by reference in its entirety; and which is a continuation of and claims priority to U.S. patent application Ser. No. 14/311,848, entitled "Breast Pump Shield," filed Jun. 23, 2014, now U.S. Pat. No. 9,408,957, which is incorporated herein by reference in its entirety.

TECHNICAL FIELD

This disclosure relates generally to breast pumps. More particularly, the disclosure made herein relates to a breast pump kit that can be easy to use, comfortable to use, and can be formed as a disposable article for purposes of convenience, sanitation, and/or other reasons.

BACKGROUND

Unless otherwise indicated herein, the details in this section are not prior art to the claims in this application and are not admitted to be prior art by inclusion in this section.

Until the middle of the twentieth century, almost all children in the world were breastfed by their mothers (or a substitute such as a wet nurse). From around the 1940's through the 1990's, the popularity and prevalence of breastfeeding decreased in the United States. In the late part of the twentieth century and over the past ten to fifteen years, breastfeeding has experienced a revival in the United States, with medical experts encouraging mothers to breastfeed children based upon a large body of scientific evidence that breastfeeding encourages healthy growth and development of children.

In modern American society, however, many mothers work outside the home or are busy with various activities that often require them to leave their homes. For many mothers, this time away from the home can be disruptive to breastfeeding schedules. Some mothers employ breast pumps to pump or express breast milk at home, at the office, or elsewhere.

Because breast milk is consumed primarily by young children, first and foremost infants of zero to six months of age and secondarily children up to about two to four years of age, some experts encourage sterilization and frequent cleaning of breast pump components. When away from the home, mothers may experience difficulty in finding a suitable place and/or equipment to thoroughly clean the breast pump components. As such, breast pumping outside the home can be difficult for mothers.

Furthermore, some women experience pain during or after breast pumping. In particular, some women experience pain as the nipples enlarge during pumping and/or from rubbing that can occur during use of a breast pump. Various approaches are used in an attempt to reduce this pain. For example, some mothers use a low setting for a breast pump at the beginning of pumping and later, after the nipple has extended and/or enlarged, the suction and/or speed of the breast pump can be increased without causing pain to the mother.

Because some breast pumps do not have variable settings, and because many mothers want to complete breast pumping as quickly as possible when away from the home, some mothers are unable to address the pain that may occur during pumping. Because of this, some mothers are discouraged from breastfeeding their children or may cease breastfeeding at the earliest opportunity.

SUMMARY

Concepts and technologies are disclosed herein for a breast pump kit. As used herein, a "breast" is used to refer only to a breast of a human female and excludes breasts of other living organisms. In some embodiments, a breast pump kit can include a breast pump shield and a leak-resistant and spill-resistant breast pump milk bag. The breast pump shield can be formed from one or more plastics, acrylics, other polymers, and/or other materials. The breast pump shield can also be formed as a disposable one-use article, as will be explained in more detail below. The breast pump shield can include a body portion and one or more covers. One or more of the covers can include multiple layers. According to various embodiments, one or more of the covers can include at least two layers, namely, a lubricant layer and a support layer. In some other embodiments, the cover can include a wiping layer. In some embodiments, the cover can include three layers, namely a support layer, a lubricant layer, and a wiping layer. In some embodiments, a layer of lubricant ("lubricant layer") also can be located within the body portion of the breast pump shield. Other covers can be included to seal and protect the breast pump shield, in some embodiments. These covers can be disposed at various locations on the breast pump shield and/or portions thereof to hermetically seal the shield from air, bacteria, dust, viruses, and/or other particles and/or liquids; to protect the lubricant from leakage and/or degradation (e.g., oxidation); and/or for other purposes. Thus, the covers can be configured to cooperate with the structure of the breast pump shield to keep the inner surfaces of the breast pump shield sanitized, lubricated, and/or otherwise ready for use.

According to various embodiments, a lubricant layer can be included on the cover and/or disposed within the breast pump shield. The lubricant can be included for various purposes. In some embodiments, the lubricant can be included to reduce irritation associated with using the breast pump shield. In particular, the lubricant can be used to lubricate surfaces that come into contact with the breasts of the user and/or portions of the breasts of the user (e.g., nipples, areola, etc.). The lubricant can be formulated in a manner that prevents thinning and/or degradation of the lubricant in high heat environments (e.g., during shipping, etc.). Furthermore, the cover can include a lubricant layer for convenience of the user. For example, a user may wipe lubricant from the cover onto her breast(s) prior to use, if desired.

The support layer can be provided to support the lubricant layer and the wiping layer, as well as to provide a hermetic seal for the breast pump shield. In some embodiments, an adhesive layer may be located at a perimeter of the cover as well for purposes of joining the cover to the breast pump shield. By joining the cover to the breast pump shield and thereby providing a hermetic seal for the breast pump shield, the cover (and/or multiple covers in cooperation with one another) can be included to ensure that the breast pump shield remains sterile. The hermetic seal also may prevent leakage of, oxidation of, and/or degradation of the lubricant layer located within the body portion. Thus, as noted above, the breast pump shield can be disposable and kept sterile and ready for use by the one or more covers. The wiping layer can be included to provide a wipe or cleaner for the user. The wiping layer can be removed from the other layers, in some embodiments, and can be used to clean up before, during, or after pumping. In some embodiments, the wiping layer can include a disinfectant and/or sterilization liquid that can be wiped by the user prior to lubrication of the breast and/or before using the breast pump shield. It should be understood that this example is illustrative and therefore should not be construed as being limiting in any way.

According to some embodiments, the breast pump shield and/or components or portions thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components or portions thereof can be formed from semi-rigid and/or soft materials such as rubber, plastic films, latex, or the like. The materials used to form the breast pump shield can be designed to provide ample rigidity while providing a lightweight disposable article. Thus, function is balanced with cost and weight. These and other aspects of the concepts and technologies will be illustrated and described herein.

According to one aspect of the concepts and technologies described herein, a breast pump kit is disclosed. The breast pump kit can include a breast pump shield. The breast pump shield can include a breast engagement portion that can be configured to receive at least a portion of a human breast, a suction chamber that can be located in proximity to the breast engagement portion, and a bag engagement portion that can include an attachment mechanism. The breast pump shield also can include a one-way valve. The breast pump also can include a breast pump milk bag. The beast pump milk bag can include a bag engagement mechanism that can be configured to cooperate with the bag engagement portion to connect the breast pump milk bag to the breast pump shield. The breast pump milk bag can be configured to receive milk from the suction chamber and via the one-way valve.

In some embodiments, the breast pump kit further can include a cover that can include a support layer. The cover can cooperate with the body portion to provide at least part of a hermetic seal for the breast pump shield prior to use. In some embodiments, the cover further can include a lubricant layer. The lubricant layer can include a layer of lubricant and the breast pump shield can be disposable. In some embodiments, the breast pump shield can include an inlet projection. The inlet projection can have a first outer diameter at a first end and a second outer diameter at a second end. The first outer diameter can be larger than the second outer diameter.

In some embodiments, the breast pump shield further can include an ergonomic handle. The ergonomic handle can include two finger grasp projections. In some embodiments, the breast pump milk bag further can include a cover assembly. In some embodiments, the cover assembly can include a valve bypass having a passageway. The valve bypass can be configured to open the one-way valve to enable selective movement of fluid between the breast pump milk bag and outside of the breast pump milk bag. In some embodiments, the cover assembly further can include a cover engagement portion having a nozzle and a nozzle cover. The cover further can include a wiping layer, and the one-way valve can include a duckbill valve. The breast pump milk bag can be leak resistant and spill resistant.

According to one aspect of the concepts and technologies described herein, another breast pump kit is disclosed. The breast pump kit can include a breast pump shield. The breast pump shield can include a breast engagement portion that can be configured to receive at least a portion of a human breast and a suction chamber that can be located in proximity to the breast engagement portion. The suction chamber can include a tapered inlet projection formed thereon and a bag engagement portion that can include an attachment mechanism. The breast pump kit also can include a one-way valve and a breast pump milk bag. The beast pump milk bag can include a bag engagement mechanism that can be configured to cooperate with the bag engagement portion to connect the breast pump milk bag to the breast pump shield. The breast pump milk bag can be configured to receive milk from the suction chamber and via the one-way valve.

In some embodiments, the breast pump kit further can include a cover that can include a support layer. The cover can cooperate with the body portion to provide at least part of a hermetic seal for the breast pump shield prior to use. In some embodiments, the breast pump shield further can include an ergonomic handle. In some embodiments, the breast pump kit further can include a cover assembly that can be configured to be attached to the breast pump milk bag. In some embodiments, the cover assembly can include a valve bypass having a passageway. The valve bypass can be configured to open the one-way valve to enable selective movement of fluid between the breast pump milk bag and outside of the breast pump milk bag. The cover assembly also can include a cover engagement portion having a nozzle and a nozzle cover.

According to another aspect of the concepts and technologies described herein, yet another breast pump kit is disclosed. The breast pump kit can include a breast pump shield. The breast pump shield can include a breast engagement portion that can be configured to receive at least a portion of a human breast, and a suction chamber that can be located in proximity to the breast engagement portion. The suction chamber can include a tapered inlet projection formed thereon and a bag engagement portion that can include an attachment mechanism. The inlet projection can have a first outer diameter at a first end and a second outer diameter at a second end. The first outer diameter can be larger than the second outer diameter. The breast pump kit also can include a one-way valve; a cover assembly; and a breast pump milk bag. The breast pump milk bag can include a bag engagement mechanism that can be configured to cooperate with the bag engagement portion to connect the breast pump milk bag to the breast pump shield. The breast pump milk bag can be configured to receive milk from the suction chamber and via the one-way valve.

In some embodiments, the breast pump kit further can include a cover that can include a support layer and a lubricant layer. The cover can cooperate with the body portion to provide at least part of a hermetic seal for the breast pump shield prior to use. In some embodiments, the breast pump shield further can include an ergonomic handle. In some embodiments, the cover assembly can include a valve bypass having a passageway. The valve bypass can be configured to open the one-way valve to enable selective movement of fluid between the breast pump milk bag and outside of the breast pump milk bag. The cover assembly also can include a cover engagement portion having a nozzle and a nozzle cover.

The foregoing summary is illustrative only and is not in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 21-25 are line drawings illustrating various views of a fitment for a breast pump milk bag, according to some example embodiments of the concepts and technologies disclosed herein.

DETAILED DESCRIPTION

Figure 1:
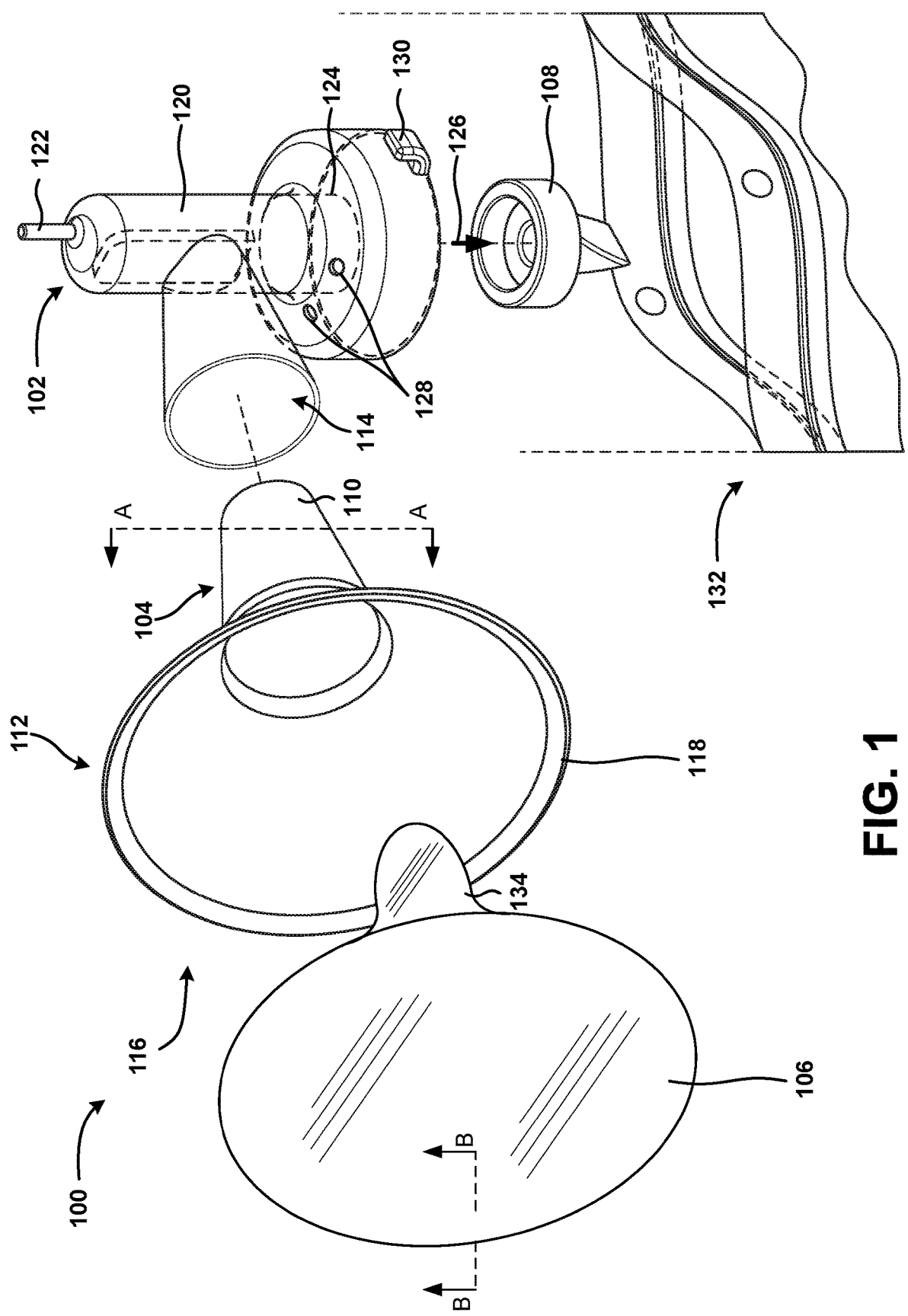
FIG. 1 is an assembly drawing of a breast pump shield, according to an illustrative embodiment of the concepts and technologies described herein.

The following detailed description is directed to breast pump shields, breast pump milk bags, and breast pump kits that can include one or more breast pump shields and/or breast pump milk bags as illustrated and described herein. A breast pump shield can be formed from a plastic or other material. The breast pump shield can also be formed as a disposable one-use article, as will be explained in more detail below. The breast pump shield can include a body portion. In some embodiments, the breast pump shield can include one or more covers. In some embodiments, one or more of the covers can include multiple layers. According to some embodiments, one or more of the covers can include one, two, three, or more than three layers. The layers can include one or more of a lubricant layer, a support layer, a wiping layer, other layers, and the like. A layer of lubricant ("lubricant layer") also can be located within the body portion of the breast pump shield, in some embodiments. The one or more covers, if included, can be disposed at various locations on the breast pump shield to hermetically seal the shield from air, bacteria, dust, viruses, and/or other particles and/or liquids; to prevent degradation, leakage, or other effects on the lubricant layer (if included); and/or for other purposes. Some embodiments of the covers can cooperate with the structure of the breast pump shield to keep the inner surfaces of the breast pump shield sanitized, lubricated, and/or otherwise ready for use.

According to various embodiments, a lubricant layer can be included on the cover and/or disposed within the breast pump shield. The lubricant can be included for various purposes. In some embodiments, the lubricant can be included to reduce irritation associated with using the breast pump shield. In particular, the lubricant can be used to lubricate surfaces that come into contact with the breasts of the user and/or portions of the breasts of the user. The lubricant can be formulated in a manner that prevents thinning and/or degradation of the lubricant in high heat environments. Furthermore, the cover can include a lubricant layer for convenience of the user. For example, a user may wipe lubricant from the cover onto her breast(s) prior to use, if desired.

The support layer can be provided to support the lubricant layer and the wiping layer, as well as to provide a hermetic seal for the breast pump shield. In some embodiments, an adhesive layer may be located at a perimeter of the cover as well for purposes of joining the cover to the breast pump shield. By joining the cover to the breast pump shield and thereby providing a hermetic seal for the breast pump shield, the cover (and/or multiple covers in cooperation with one another) can be included in some embodiments to ensure that the breast pump shield remains sterile. The hermetic seal also may prevent leakage of, oxidation of, and/or degradation of the lubricant layer located within the body portion and/or elsewhere as noted above. Thus, as noted above, the breast pump shield can be disposable and kept sterile and ready for use by the one or more covers. The wiping layer can be included to provide a wipe, cleanser, or cleaner for the user. The wiping layer can be removed from the other layers, in some embodiments, and can be used to clean up before, during, or after pumping. In some embodiments, the wiping layer can include a disinfectant and/or sterilization liquid that can be wiped by the user prior to lubrication of the breast and/or before using the breast pump shield. It should be understood that this example is illustrative and therefore should not be construed as being limiting in any way.

According to some embodiments, the breast pump shield and/or components thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components thereof can be formed from semi-rigid and/or soft materials such as rubber, plastic films, silicone, latex, or the like. The materials used to form the breast pump shield can be designed to provide ample rigidity while providing a lightweight disposable article. Thus, function can be balanced with cost and weight.

Various embodiments disclosed herein are also directed to various embodiments of a breast pump milk bag. In some embodiments, the breast pump milk bag can include a sealable bag with attachment mechanisms for connecting to the breast pump shield. In some embodiments, for example, the breast pump shield can include hooks that can interact with the attachment mechanisms to hold the breast pump milk bag in place before, during, and/or after lactation. In some other embodiments, the breast pump shield can include a threaded portion that can engage the breast pump milk bag via reciprocal threads formed on the breast pump milk bag to hold the breast pump milk bag in place before, during, and/or after lactation. In some embodiments, the breast pump shield includes a one way valve that can allow milk to enter the breast pump milk bag but not to exit the breast pump milk bag unless the one way valve is opened. In some embodiments, the functionality of the one way valve can be provided by a duckbill valve, which can be opened by pressure created by the breast pump to allow breast milk to pass through the one way valve and into the breast pump milk bag.

Upon disconnection of the breast pump, the one way valve can be configured to remain closed, thereby preventing leakage and/or spillage of the breast milk from the bag. The breast pump milk bag can also include a cover. The cover can include a cover passageway that can be configured to penetrate the one way valve (e.g., to create a passageway through the one way valve) thereby allowing milk to be controllably removed from the breast pump milk bag. The cover can include an engageable cover for the passageway, thereby preventing leaking and/or spillage from the breast pump milk bag through the passageway. These and other aspects of the concepts and technologies disclosed herein will be illustrated and described in more detail below.

In the following detailed description, references are made to the accompanying drawings that form a part hereof, and in which are shown by way of illustration specific embodiments or examples. It must be understood that the disclosed embodiments are merely illustrative of the concepts and technologies disclosed herein. The concepts and technologies disclosed herein may be embodied in various and alternative forms, and/or in various combinations of the embodiments disclosed herein. The word "illustrative," as used in the specification, is used expansively to refer to embodiments that serve as an illustration, specimen, model or pattern.

Additionally, it should be understood that the drawings are not necessarily to scale, and that some features may be exaggerated or minimized to show details of particular components. In other instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to variously employ the present disclosure. Referring now to the drawings, in which like numerals represent like elements throughout the several figures, aspects of breast pump shields will be presented.

Referring first to FIG. 1, aspects of a breast pump shield 100 according to various embodiments of the concepts and technologies described herein will be described in detail. In particular, FIG. 1 illustrates one illustrative embodiment of a breast pump shield 100. It should be understood that the illustrated and described illustrative embodiment of the breast pump shield 100 shown in FIG. 1 is one illustrative embodiment of the concepts and technologies described herein, and therefore should not be construed as being limiting in any way of the concepts and technologies described herein.

In some embodiments, as shown in FIG. 1, a breast pump shield 100 can include a breast pump shield main body portion ("body portion") 102, a funnel portion 104, a cover 106, and a valve attachment 108. The funnel portion 104 can be shaped to receive and/or engage a breast during lactation. According to various embodiments of the concepts and technologies described herein, the funnel portion 104 can include a neck portion 110 and a breast engagement portion 112. According to various embodiments, the neck portion 110 can be received by a funnel insertion portion 114 of the body portion 102.

Thus, it can be appreciated that the body portion 102 can be configured to act as a backbone of sorts of the breast pump shield 100. Thus, the body portion 102 can be designed to support other components of the breast pump shield 100. As will be illustrated and described in more detail below, the body portion 102 can have various configurations and/or features. As such, the illustrated and described example embodiment shown in FIG. 1 is merely illustrative of the concepts and technologies described herein and should not be construed as being limiting in any way.

According to various embodiments, the funnel portion 104 can be connected to the body portion 102 via a connection mechanism formed at the neck portion 110 and the funnel insertion portion 114. In some embodiments, the connection mechanism can include a pressure fit formed between the neck portion 110 and the funnel insertion portion 114. Thus, it can be appreciated that at least a portion of the outside diameter of the neck portion 110 can be slightly larger than at least a portion of the inside diameter of the funnel insertion portion 114, though this is not necessarily the case. Although not shown in FIG. 1, it should be understood that the neck portion 110 and/or the funnel insertion portion 114 can include ribs, threads, and/or other structures to create a connection between the body portion 102 and the funnel portion 104 and/or for other purposes. It should be understood that this example is illustrative and therefore should not be construed as being limiting in any way.

The breast engagement portion 112 of the funnel portion 104 can be shaped and/or configured to receive and/or engage an outer surface of a breast of a user. The breast engagement portion 112 also can be configured to center a nipple of the breast within the breast engagement portion 112 during lactation/suction and/or to encourage the nipple of the breast to enter a suction and/or stimulation chamber, as will be explained in more detail below. It can be appreciated that during lactation, the nipple of the user may enlarge and move into the inside of the neck portion 110 and/or the funnel insertion portion 114. It should be understood that this example is illustrative and therefore should not be construed as being limiting in any way.

According to various embodiments, a breast or a portion thereof can be inserted into the breast engagement portion 112 via an open end 116. The open end 116 can be defined, in some embodiments, by a ring 118 of material located at the open end 116. The ring 118 can engage the breast or chest of the user and the breast or areola of the user can be engaged within the breast engagement portion 112, or a portion thereof. The nipple of the breast can pass through the breast engagement portion 112 and into a stimulation and/or suction chamber or region formed by the neck portion 110, as noted above. In the illustrated embodiment, the stimulation chamber or region is provided by a neck portion 110 and the funnel insertion portion 114 as explained above. It should be understood that this example is illustrative and therefore should not be construed as being limiting in any way.

As mentioned above, the neck portion 110 can be configured to accommodate and/or engage the nipple during lactation. Thus, although not shown in FIG. 1, an inside surface of the neck portion 110 can include ribs, ridges, and/or other structures to stimulate milk production and/or lactation during use of the breast pump shield 100. In various embodiments, the neck portion 110 can be configured as a cylindrical passageway. The neck portion 110 can be tapered, in some embodiments, though this is not necessarily the case. During pumping, the nipple can extend to or even into the neck portion 110.

According to various embodiments, the extension of the nipple into, through, or within the neck portion 110 can occur repeatedly with the application of suction to the neck portion 110. The movement and/or extension of the nipple within the neck portion 110 can encourage and/or stimulate milk flow, as generally is understood. The body portion 102 also can include a suction chamber, structure, or region ("suction chamber") 120. Air pressure within the suction chamber 120 can be controlled and/or regulated by a breast pump (not visible in FIG. 1), which can be connected to the suction chamber 120 via a hose, connector, or other structure. The hose, connector, or other structure can be connected to or inserted into the suction chamber 120 via an inlet 122. Thus, the breast pump or other device can control air pressure within the suction chamber 120, the neck portion 110, and/or the breast engagement portion 112 via connection through the inlet 122.

The suction chamber 120 also can be formed by a valve attachment 108. The valve attachment 108 can attach to a ring 124 formed as part of the body portion 102. As is generally understood, the valve attachment 108 can be configured to allow one-way fluid flow from within the suction chamber 120 to outside of the suction chamber 120. According to various embodiments of the concepts and technologies disclosed herein, the valve attachment 108 can be opened by pressure from a breast pump (e.g., positive pressure in the suction chamber 120), though this is not necessarily the case. Specifically, a fluid (e.g., air, milk, etc.) can flow from within the suction chamber 120 to outside of the valve attachment 108 along a flow path 126, but fluid (e.g., air, milk) cannot flow back into the suction chamber 120 from outside of the valve attachment (against the flow path 126). Thus, it can be appreciated that flow of fluids (air and/or liquids) in a reverse direction along the flow path 126 can be prevented or at least restricted by the valve attachment 108. Thus, the breast pump shield 100 can be shaped and configured to prevent reverse flow of milk, air, and/or contaminants from within the suction chamber 120 to a hose or other structure connected to the inlet 122. It should be understood that this example is illustrative and therefore should not be construed as being limiting in any way.

The body portion 102 also can include one or more vents 128. The vents 128 can be positioned outside of the ring 124. Thus, if a bottle (not shown in FIG. 1) or bag is attached to the body portion 102, the vents 128 can allow air pressure to escape from within the bottle or bag, thereby allowing fluid to more easily flow into the bottle or bag than would be possible without the vents 128. It should be understood that this example is illustrative and therefore should not be construed as being limiting in any way.

According to various embodiments, the body portion 102 and/or one or more portions thereof can include a lubricant layer (not visible in FIG. 1). In the illustrated embodiment, at least portions of the breast engagement portion 112 and the neck portion 110 include the lubricant layer. In some embodiments, the suction chamber 120, the inlet 122, other portions of the breast pump shield 100 and/or portions thereof can include the lubricant layer. The lubricant layer will be illustrated and described in more detail below. Additionally, the cover 106 will be illustrated and described in more detail below.

Figure 8:
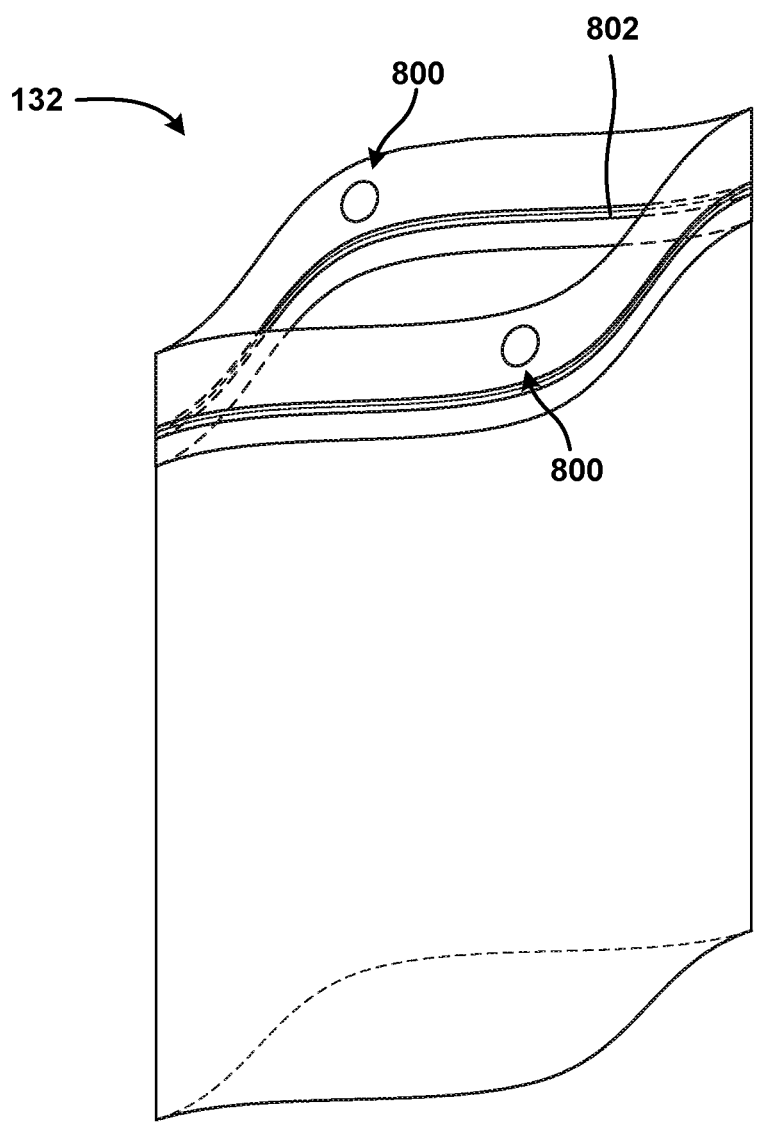
FIG. 8 is a perspective view of a milk bag for use with a breast pump shield, according to an illustrative embodiment of the concepts and technologies described herein.

According to various embodiments, the body portion 102 also can include one or more hooks 130. While only one hook 130 is visible in FIG. 1 (a second hook 130 is out of view), it should be understood that one, two, three, or more than three hooks 130 can be included on the breast pump shield 100. The hooks 130 can be used to hold, position, and/or retain a bag or other receptacle ("milk bag") 132 at a location at which milk from the suction chamber 120 can flow into the breast pump milk bag 132. Another view of the breast pump milk bag 132 is shown in FIG. 8.

In some embodiments, the hooks 130 can be used to hold a retention mechanism such as a rubber band, elastic band, clip, or the like, which can be used to retain a bottle in position without requiring threads on the inside of the body portion 102. Thus, it can be appreciated that the body portion 102 can be configured for use with bags and bottles of various configurations, thereby enabling universal (or nearly universal) use of the breast pump shield 100 with bottles, bags, and/or other milk receptacles.

Components of the breast pump shield 100 can be formed from various materials. According to various embodiments, the body portion 102 of the breast pump shield 100 and/or components of the body portion 102 such as the breast engagement portion 112, the ring 118, the neck portion 110, and/or the suction chamber 120 can be formed from one or more plastics, one or more thermoplastics, one or more acrylics, one or more resins, one or more polymers or copolymers, other (non-plastic and non-polymer) materials, and/or combinations thereof. According to some embodiments, the body portion 102 of the breast pump shield 100 can be formed using various manufacturing processes such as injection molding processes, three dimensional printing processes, machining processes, forging processes, combinations thereof, or the like. The material used to form the breast pump shield 100 can be lightweight yet rigid, thereby reducing weight, cost, and waste associated with the breast pump shield 100. The breast pump shield 100 can be disposable and designed for a single use. Because other materials and/or processes can be used to form the body portion 102 and/or other components of the breast pump shield 100, it should be understood that these examples are illustrative and therefore should not be construed as being limiting in any way.

In some embodiments, as can be seen in FIG. 1, the cover 106 can include a finger grip, tab, protrusion, or other structure ("tab") 134. The tab 134 can be used to provide a grip for a user to grasp the cover 106. Using the tab 134, the user can detach the cover 106 from the breast pump shield 100. It can be appreciated that in various embodiments, the cover 106 can be attached to the breast pump shield 100 using an adhesive. Thus, the cover 106 can be peeled away from the breast pump shield 100, in some embodiments, as generally is understood. Because the tab 134 can be optional and/or can be replaced by additional and/or alternative structures or devices, the tab 134 is not shown in the other FIGURES. It should be understood that the tab 134 or other structures or devices can be included in some, all, or none of the illustrated embodiments, and as such, the illustrated embodiments that omit the tab 134 are merely illustrative and should not be construed as being limiting in any way.

In some embodiments, the cover 106 can be configured such that the cover 106 can enwrap the entire breast pump shield 100 or a component thereof. For example, in some embodiments, the cover 106 can enwrap the entire breast pump shield 100, the entire body portion 102, the entire neck portion 110, and/or other components of the breast pump shield 100. In some embodiments, the components of the breast pump shield 100 can be enwrapped or enclosed by the cover 106 and/or multiple covers 106, so a user can unwrap the components and assemble the sterile and lubricated components together. For example, the cover 106 can be located at the ring 118, and the entire breast pump shield 100 can then be enclosed in an outer wrapper (e.g., a plastic or cellophane bag, etc.). In some other embodiments, the entire breast pump shield 100 can be unwrapped, and then can be used as a sterile and lubricated breast pump shield. Thus, the embodiments shown in the FIGURES, wherein the cover 106 covers only a portion of the breast pump shield 100 should be understood as being illustrative of some contemplated embodiments and should not be construed as being limiting in any way.

The breast pump shield 100 shown in FIG. 1 has been described as including one cover 106, one breast engagement portion 112, one neck portion 110, one suction chamber 120, one inlet 122, and two hooks 130. It should be understood, however, that some embodiments of the breast pump shield 100 can include zero, one, or more than one cover 106; zero, one, or more than one suction chamber 120; zero, one, or more than one inlet 122; and/or zero, one, two, or more than two hooks 130. In one contemplated embodiment, for example, the breast pump shield 100 can include a truncated breast engagement portion or can omit the breast engagement portion 112 altogether, thereby resulting in a short and compact breast pump shield 100 that essentially consists of the neck portion 110 and the suction chamber 120. It should be understood that this example is illustrative and therefore should not be construed as being limiting in any way.

Figure 3:
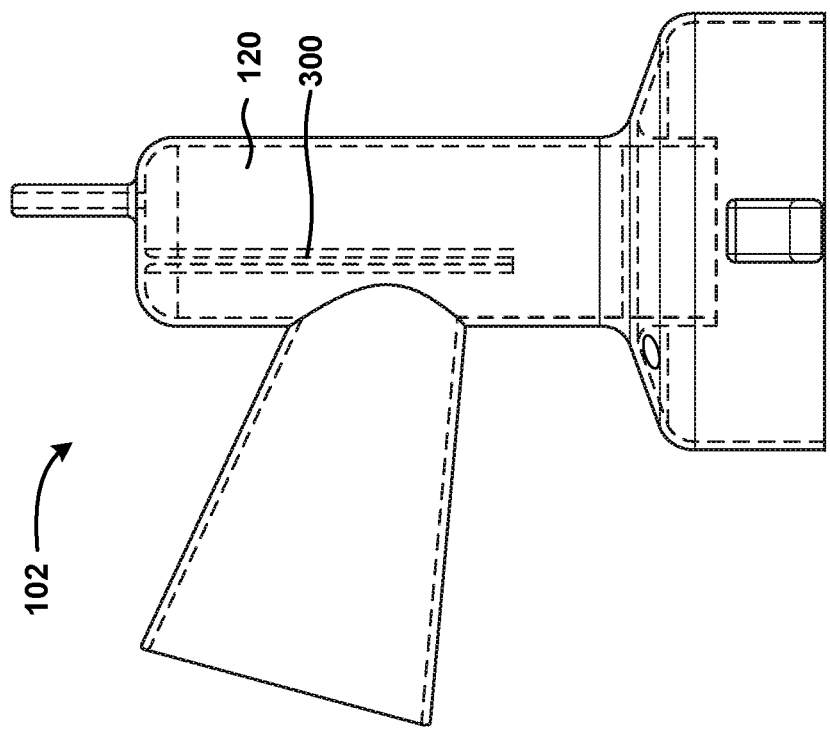
FIG. 3 is a side view of a body portion of a breast pump shield, according to an illustrative embodiment of the concepts and technologies described herein.
Figure 2:
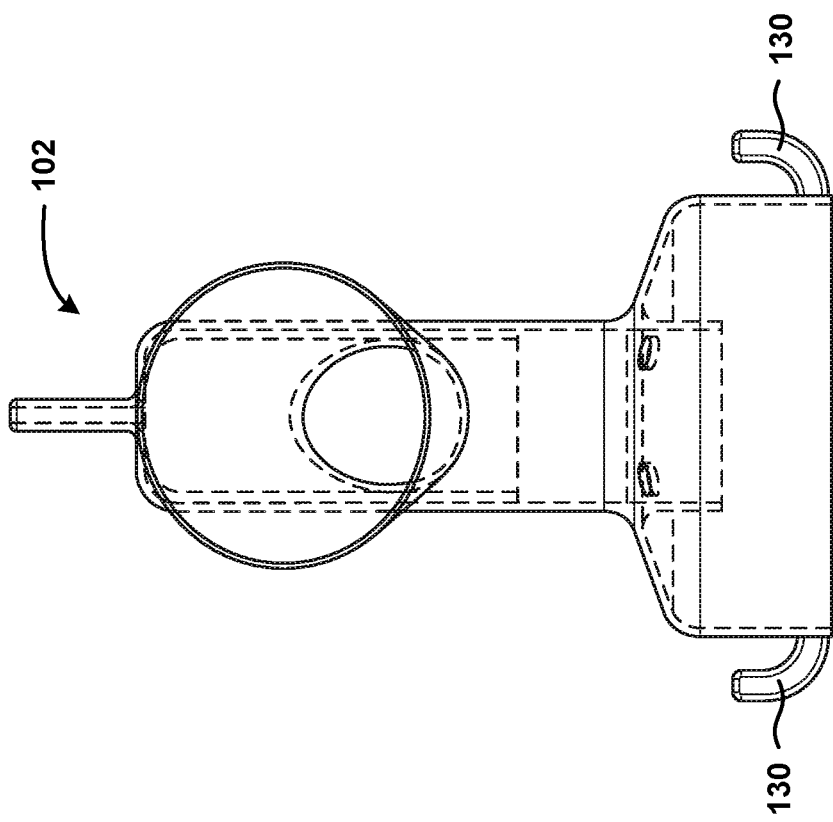
FIG. 2 is a front view of a body portion of a breast pump shield, according to an illustrative embodiment of the concepts and technologies described herein.
Figure 4:
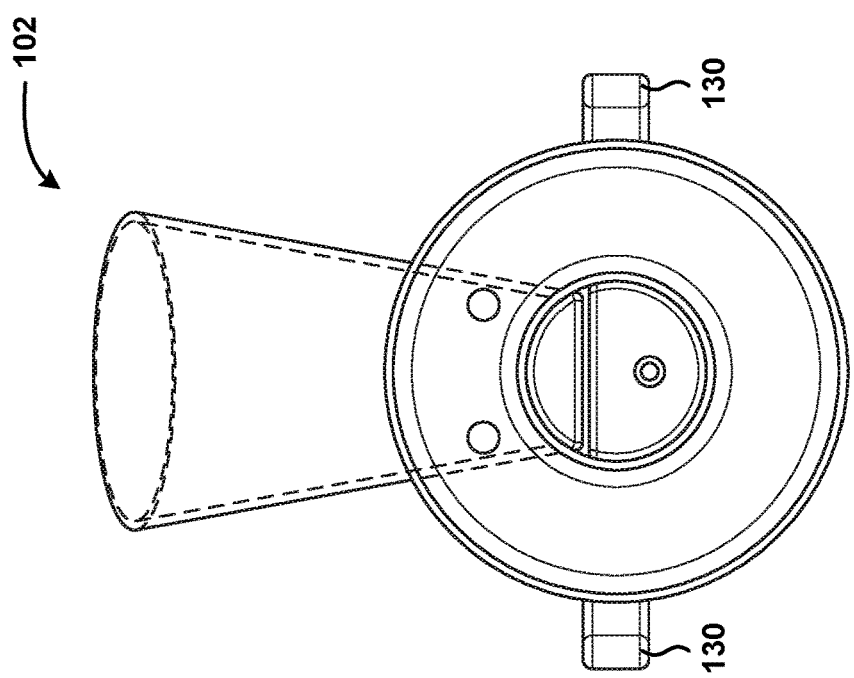
FIG. 4 is a bottom view of a body portion of a breast pump shield, according to an illustrative embodiment of the concepts and technologies described herein.

FIGS. 2-4 illustrate additional views of the body portion 102 of the breast pump shield 100. These views are provided to illustrate additional details of the structure of the body portion 102, most of which has been discussed above with reference to FIG. 1. As visible in FIG. 3, the suction chamber 120 of the body portion 102 can be divided or sectioned by a divider 300. The divider 300 can prevent milk from squirting out of the breast and into a proximity of the inlet 122, from which location the milk could more easily enter the inlet 122 and/or a hose attached to the inlet 122. Thus, the divider 300 can be included to reduce the chances of contamination of the breast pump hose (not visible in the FIGURES) and/or other structures. It should be understood that this example is illustrative and therefore should not be construed as being limiting in any way.

Figure 5:
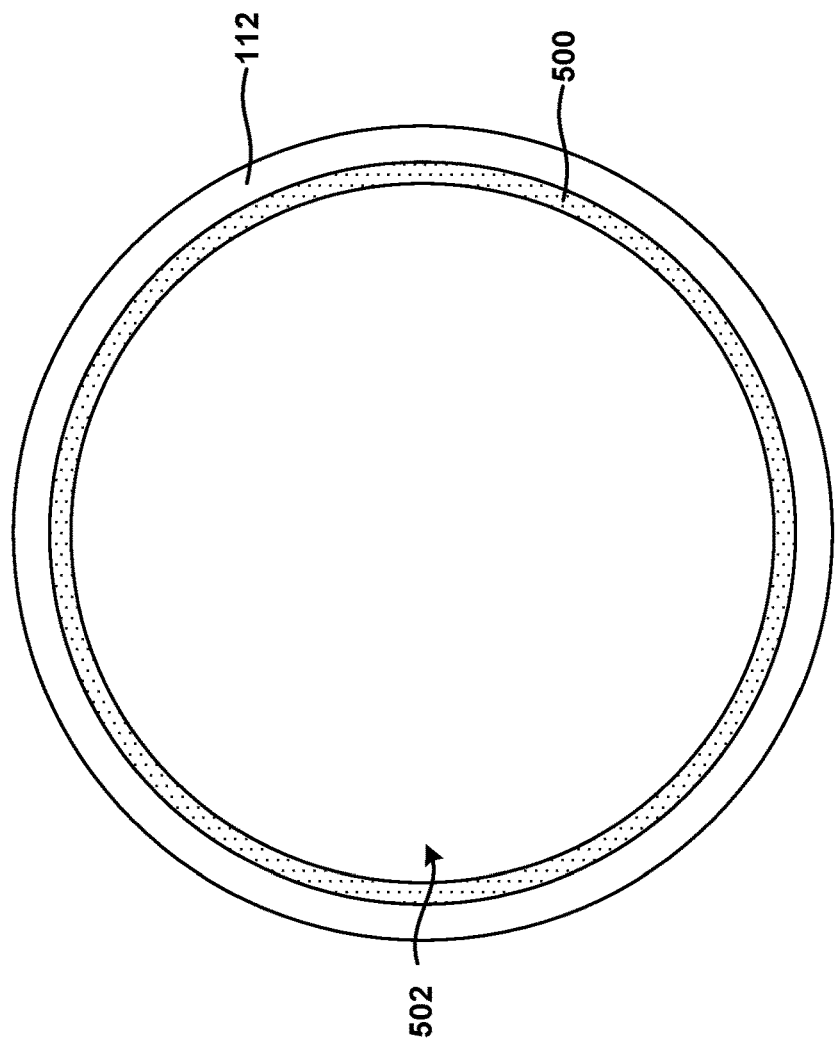
FIG. 5 is a line drawing illustrating additional features of a breast pump shield, according to some illustrative embodiments of the concepts and technologies described herein.

Turning now to FIG. 5, additional aspects of the concepts and technologies described herein for a breast pump shield will be described in detail. In particular, FIG. 5 is a line drawing illustrating cut-away view of the neck portion 110 of the breast pump shield 100 as viewed from the cut-line A-A shown in FIG. 1, according to some illustrative embodiments of the concepts and technologies described herein. It should be understood that this example is illustrative and therefore should not be construed as being limiting in any way.

As can be seen in FIG. 5, the neck portion 110 can include a lubricant layer 500 disposed within the neck portion 110. In some embodiments, the lubricant layer 500 can be located between an inner surface (not labeled in FIG. 5) of the neck portion 110 and a void 502 of the neck portion 110. As mentioned above, it can be appreciated that the void 502 can accommodate a nipple of a lactating mother during pumping and/or use of the breast pump shield 100. As such, in some embodiments the lubricant layer 500 can be included to lubricate the inner surface of the neck portion 110. The lubricant layer 500 can be included to prevent irritation of the nipples, which can result from pumping. Similarly, the lubricant layer 500 can be included to reduce pain, which some women may experience when pumping. Still further, the lubricant layer 500 can be included to allow the nipple to slide up and down along the side wall of the neck portion 110, which can stimulate the nipples and encourage milk flow. It should be understood that these examples are illustrative and therefore should not be construed as being limiting in any way.

The functionality of the lubricant layer 500 can be provided, in some embodiments, by a food grade and/or hypoallergenic lubricant. Thus, the lubricant layer 500 can be safe for use during lactation as any amounts (trace or otherwise) that pass into the expressed or pumped breast milk may not pose a risk to an infant, toddler, or other child or children who consume the milk produced using the breast pump shield 100. According to one contemplated embodiment, the lubricant used to provide the lubricant layer 500 can include a coconut-based lubricant. According to another contemplated embodiment, the lubricant used to provide the lubricant layer 500 can include a palm-based lubricant. According to another embodiment, the lubricant used to provide the lubricant layer 500 can include a fruit-based or vegetable-based lubricant such an olive-oil-based lubricant, a vegetable-oil-based lubricant (e.g., canola oil, soy oil, peanut oil, corn oil, avocado oil, safflower oil, sunflower oil, etc.), nut oils (e.g., almond oil, walnut oil), other oils (e.g., cottonseed oil, sunflower oil, etc.) combinations thereof, or the like. According to other embodiments, the lubricant used to provide the lubricant layer 500 can include other oils and/or lubricants such as petroleum based and/or mineral-based lubricants. According to still other embodiments, the lubricant used to provide the lubricant layer 500 can include flax oil or fish oil, which can be high in Omega-5 fatty acids that are known to encourage healthy brain development of infants. Thus, oil that leaks into the milk can actually be beneficial for the infant, in some embodiments. Because other oils and/or lubricants can be used, it should be understood that the above examples are illustrative and therefore should not be construed as being limiting in any way.

According to various embodiments, the lubricant layer 500 can be provided by a thick heat-resistant lubricant. As such, during shipping and/or other transportation of the breast pump shield 100, the lubricant layer 500 may not move or run from an original location. This functionality can be particularly useful when shipping the breast pump shield 100 in a high heat environment, or the like. As such, the breast pump shield 100 can be ready for use without applying lubricant to the breast pump shield 100, a component thereof, and/or a nipple or breast of the lactating mother. In some embodiments, the lubricant or oil used to provide the lubricant layer 500 can be thickened using various processes to prevent running and/or melting of the lubricant. It should be understood that this example is illustrative and therefore should not be construed as being limiting in any way.

Figure 6A:
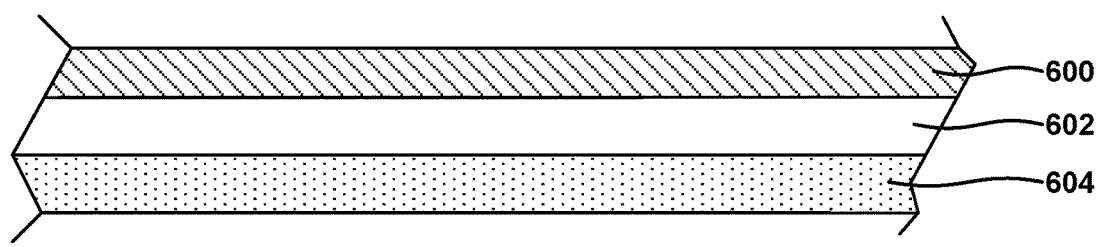
FIGS. 6A-6B are line drawings illustrating additional features of a breast pump shield cover, according to some illustrative embodiments of the concepts and technologies described herein.
Figure 6B:
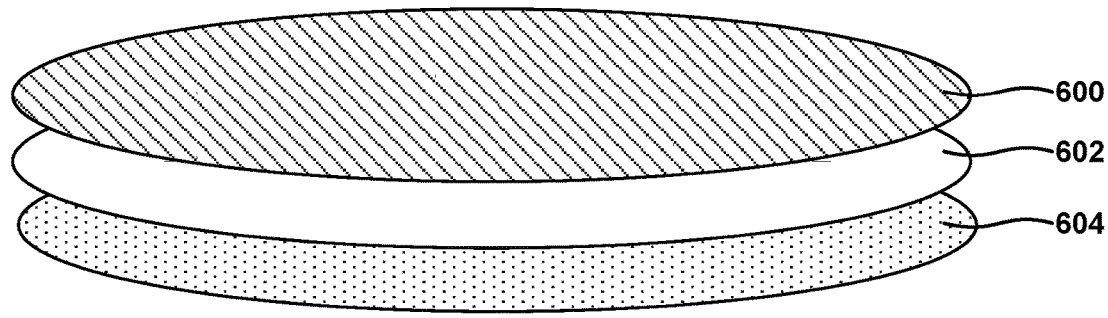

Referring now to FIGS. 6A-6B, additional aspects of the concepts and technologies described herein for a breast pump shield 100 will be described in detail. In particular, FIG. 6A illustrates a cross section of the cover 106, viewed along the cut/view line B-B shown in FIG. 1. It can be appreciated that a cross section view of any portion of the cover 106 can be substantially similar to the view shown in FIG. 6A. Additionally, FIG. 6B illustrates an assembly drawing of the cover 106. Collective reference will be made to FIGS. 6A-6B to describe the cover 106 and/or the components thereof.

As shown in FIGS. 6A-6B, the cover 106 can include multiple layers. According to various embodiments of the concepts and technologies described herein, the cover 106 can include two or more layers. According to some other embodiments, the cover 106 can include three or more layers. In the illustrated embodiment, the cover 106 includes three layers. Based upon the foregoing, it can be appreciated that the illustrated embodiment is illustrative and therefore should not be construed as being limiting in any way.

The cover 106 shown in FIGS. 6A-6B includes a wiping layer 600, a support layer 602, and a lubricant layer 604. According to various embodiments, the lubricant layer 604 can be provided by a lubricant that may be similar or even identical to the lubricant layer 500 illustrated and described above with reference to FIG. 5, though this is not necessarily the case. Thus, it can be appreciated that according to some embodiments of the concepts and technologies described herein, the lubricant layer 604 can be provided by a coconut-based lubricant, a palm-based lubricant, a shea-based lubricant, a petroleum-based lubricant, a nut-based lubricant, a fruit-based lubricant, a vegetable-based lubricant, a mineral-oil-based lubricant, other oils and/or lubricants, combinations thereof, or the like. Because the lubricant layer 604 can be provided by other lubricants, it should be understood that the above examples are illustrative and therefore should not be construed as being limiting in any way.

In some embodiments, the lubricant layer 604 can be thickened as explained above with reference to the lubricant layer 500. The lubricant layer 604 can be applied by a user to her nipples, areolas, and/or other parts of her breast to reduce friction, rubbing, and/or pain associated with pumping the breasts during milk production. As noted above, the lubricant layer 604 can be included to obviate the user from needing additional lubricant. As such, it can be appreciated that the lubricant layer 604 can be included to provide extra lubricant that may or may not be used by a user. In still other embodiments, the cover 106 can include the lubricant layer 604 so a user can rub the cover on the breasts and/or parts of the breast or on the breast pump shield 100 and/or components thereof to further lubricate the breasts and/or breast pump shield 100 as described herein. It should be understood that this example is illustrative and therefore should not be construed as being limiting in any way.

The support layer 602 can be provided to add strength and/or support to the cover 106, in some embodiments. In particular, in some embodiments, the support layer 602 can be provided by a layer, sheet, or piece of a metal foil, a plastic sheet, a polymer layer, and/or another substrate or material. In addition to and/or instead of providing rigidity and/or support for the cover 106, the support layer 602 can, in some embodiments, provide a hermetic seal for the breast pump shield 100 to keep the breast pump shield sanitary and/or sterile. The support layer 602 also can be configured to prevent leakage of, oxidation of, and/or other degradation of the lubricant layer 500 and/or the lubricant layer 604 illustrated and described herein. In one contemplated embodiment, the support layer 602 is provided by a metal foil layer. It should be understood that this example is illustrative and therefore should not be construed as being limiting in any way.

According to some embodiments, the wiping layer 600 can be provided by a natural or synthetic fiber cloth layer. In particular, some embodiments of the wiping layer 600 include a cotton fiber layer, while some other embodiments of the wiping layer 600 are provided by synthetic fiber layer. The wiping layer 600 can be included for the convenience of the user.

In particular, the wiping layer 600 can be used as a napkin, towel, or the like, for cleaning the breast before, during, or after pumping. For example, the wiping layer 600 can be used to wipe lubricant off of the breast, to wipe milk off of the breast, to clean hands, fingers, or the like, and/or to wipe or clean other surfaces. In some contemplated embodiments, the wiping layer 600 can be joined to the support layer 602 using an adhesive. As such, in some embodiments a user can peel the wiping layer 600 away from the support layer 602. It can be appreciated that the support layer 602 can prevent the wiping layer 600 from absorbing and/or touching the lubricant layer 604. It should be understood that these examples are illustrative and therefore should not be construed as being limiting in any way.

It can be appreciated from the above description of the cover 106 that the breast pump shield 100 can be ready for use. Thus, some embodiments of the concepts and technologies described herein are used to provide a disposable and/or travel breast pump shield 100 that does not require cleaning prior to use for pumping. Furthermore, embodiments of the concepts and technologies described herein provide a sterile and ready to use breast pump shield that requires no additional cleaning and/or lubrication prior to or after use, thereby providing a truly portable and/or disposable breast pump shield 100. It should be understood that these examples are illustrative and therefore should not be construed as being limiting in any way.

Although not visible in the FIGURES, it should be understood that the cover 106 and/or other covers for the breast pump shield 100 can include an adhesive layer. The adhesive layer can be disposed on the support layer 602 and/or on other layers or portions of the cover 106. In some contemplated embodiments, the adhesive is disposed about a ring of the support layer 602. In some embodiments, the adhesive can be disposed in a ring that substantially corresponds to a location of the ring 118 shown in FIG. 1. In some embodiments, the lubricant layer 604 does not extend to or onto the adhesive layer. Thus, the lubricant layer 604 can be configured not to interfere with the adhesive layer, in some embodiments. In some embodiments, the adhesive layer is releasable and/or re-sealable. Thus, some embodiments of the adhesive layer can allow the user to attach and/or detach the cover 106 from the breast pump shield 100. It should be understood that these examples are illustrative and therefore should not be construed as being limiting in any way.

Figure 7:
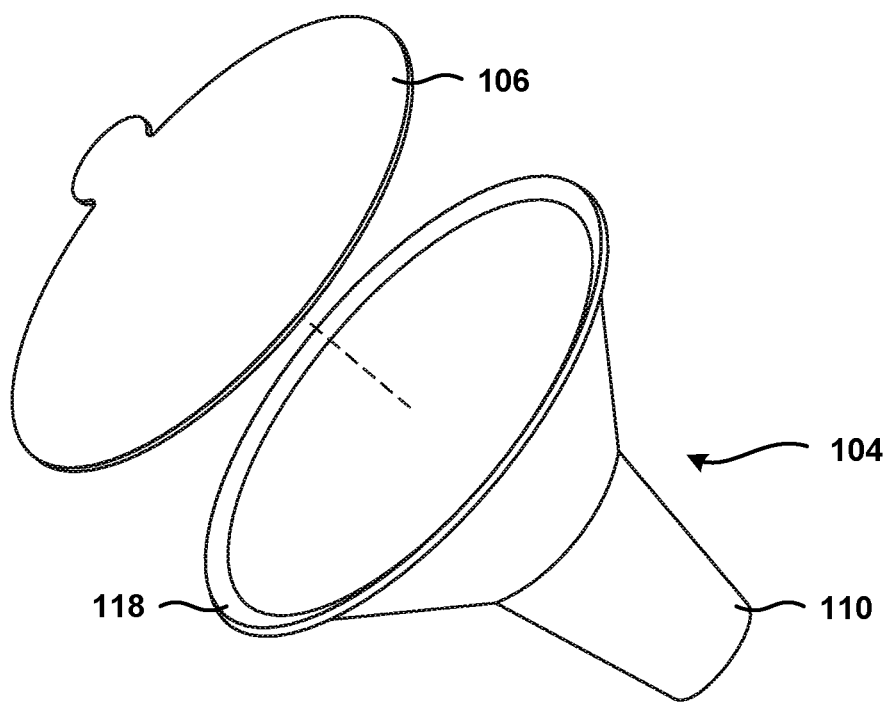
FIG. 7 is a perspective view of a funnel portion and cover of a breast pump shield, according to an illustrative embodiment of the concepts and technologies described herein.

FIG. 7 illustrates an assembly drawing of a cover 106 and a funnel portion 104. The cover 106 can be disposed to the ring 118 of the funnel portion 104, as mentioned above with reference to FIG. 1. Although not shown in FIG. 7, it should be understood that another cover can be located at the opposite end of funnel portion 104 (e.g., at the end of the neck portion 110), thereby sealing the funnel portion 104 and providing the funnel portion 104 with a hermetic seal. Furthermore, as explained above with reference to FIG. 1, a lubricant can be located within the funnel portion 104, if desired.

FIG. 8 illustrates a perspective view of a breast pump milk bag 132 according to one illustrative embodiment of the concepts and technologies described herein. As can be seen in FIG. 8, the breast pump milk bag 132 can include apertures 800. The apertures 800 can be used to connect the breast pump milk bag 132 to the hooks 130 of the body portion 102. This can conveniently locate the breast pump milk bag 132 in a position at which milk can be received without requiring screwing a bottle onto the body portion 102 and/or other structures. As shown in FIG. 8, the breast pump milk bag can include a seal 802. According to various contemplated embodiments, the seal 802 can be provided by a zip-style seal, mechanical fasteners, adhesives, heat-activated seals, combinations thereof, or the like. The seal 802 can be used to seal the breast pump milk bag 132 after pumping to prevent spillage and/or leakage of the milk in the breast pump milk bag 132. It should be understood that these examples are illustrative and therefore should not be construed as being limiting in any way.

Figure 9:
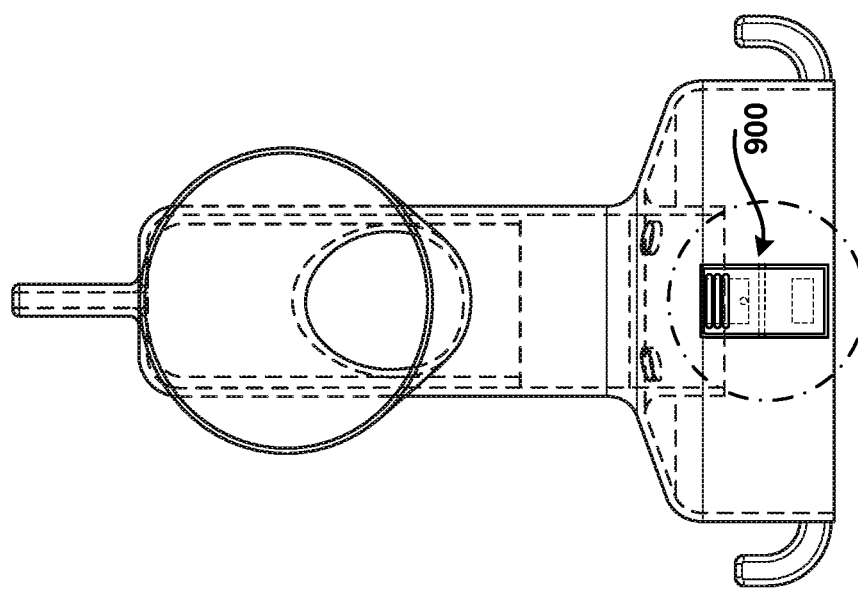
FIG. 9 is a line drawing illustrating additional features of a breast pump shield, according to some other illustrative embodiments of the concepts and technologies described herein.

Turning now to FIG. 9, additional aspects of the concepts and technologies described herein will be described. In particular, FIG. 9 shows an example embodiment of a universal or nearly-universal bottle thread attachment mechanism ("thread attachment mechanism") 900. Although the body portion 102 is illustrated in FIG. 9 as including only one thread attachment mechanism 900, it should be understood that the body portion 102 can include multiple thread attachment mechanisms 900. In one contemplated embodiment, for example, four thread attachment mechanisms 900 are distributed radially around the body portion 102 (e.g., one or more the hooks 130 can be substituted for the thread attachment mechanisms 900 and/or the thread attachment mechanisms 900 and the hooks 130 can both be distributed radially and therefore may both be included). According to one embodiment, two hooks 130 are located as shown in FIG. 9 (e.g., distributed radially one hundred eighty degrees apart), and the thread attachment mechanisms can be distributed radially (ninety degrees apart and forty five degrees offset from the hooks 130). It should be understood that this example is illustrative and therefore should not be construed as being limiting in any way.

Figure 10:
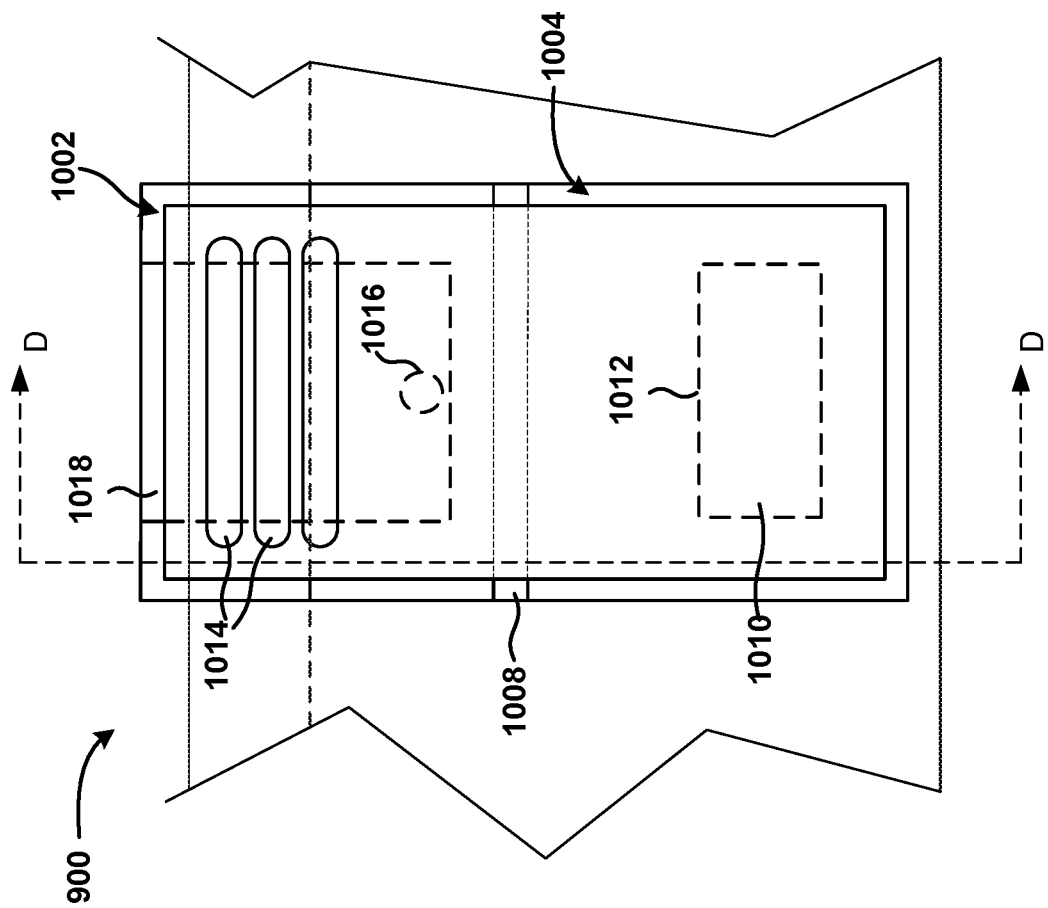
FIG. 10 is an expanded view of a universal thread attachment mechanism for a breast pump shield, according to an illustrative embodiment of the concepts and technologies described herein.
Figure 11:
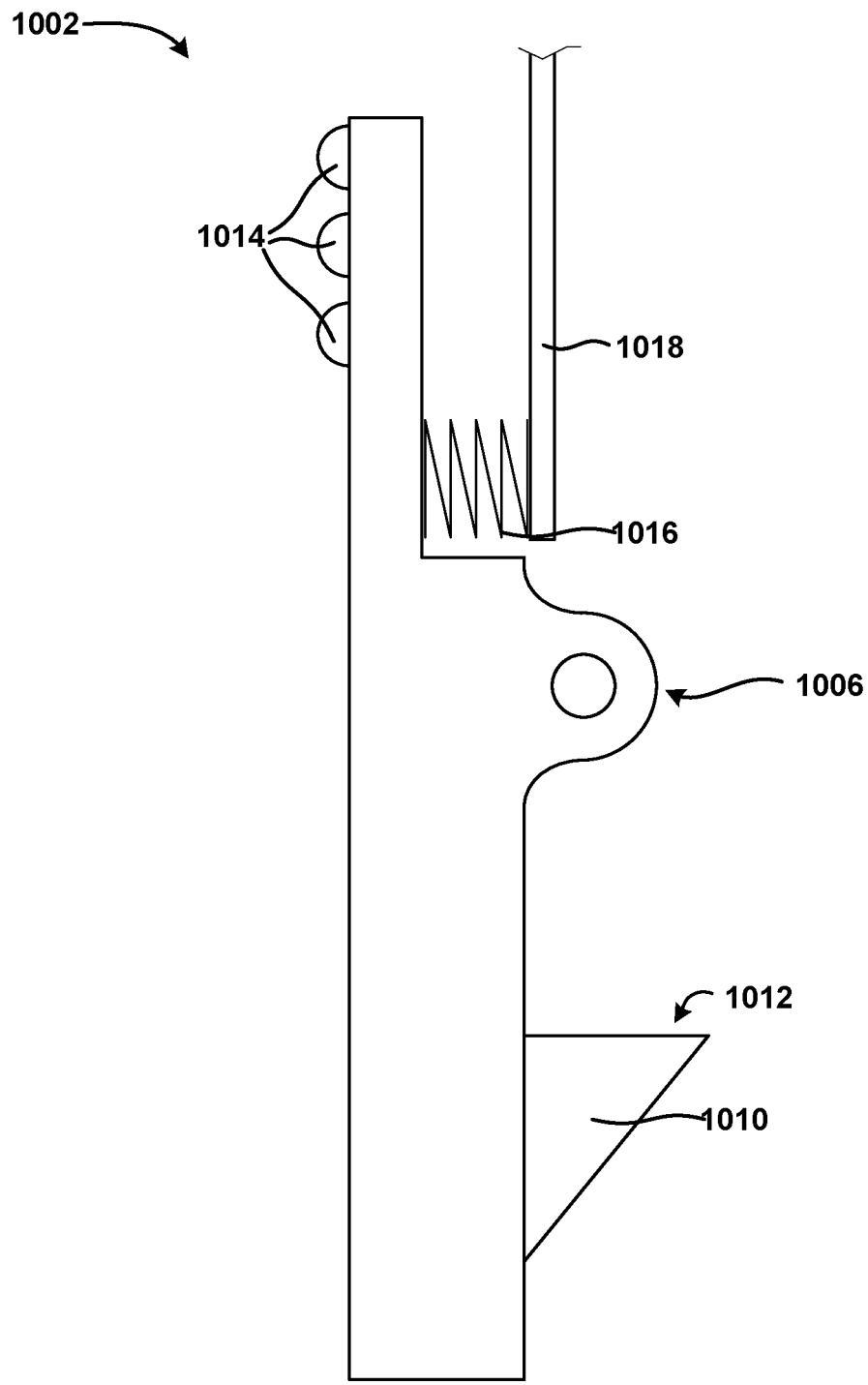
FIG. 11 is a line drawing showing additional features of the universal thread attachment mechanism as viewed along view line D-D in FIG. 10, according to an illustrative embodiment of the concepts and technologies described herein.

In some embodiments, the thread attachment mechanism 900 can be spring loaded, as will be more clearly understood with reference to FIGS. 10-11. In some other embodiments, the thread attachment mechanism 900 may not be spring loaded. In yet other embodiments, the thread attachment mechanism 900 can be provided with spring by the material used to form the breast pump shield 100 and as such, separate springs may not be included. It should be understood that these examples are illustrative and therefore should not be construed as being limiting in any way.

It should be understood that the illustrated embodiment of the thread attachment mechanism 900 is only one contemplated embodiment of a suitable structure for connecting the breast pump shield 100 to a bottle or other receptacle. Other contemplated embodiments include the use of a thread adapter that can be provided to connect one type of threads to another type of threads. Such a thread adapter may screw onto or into threads formed on the body portion 102 and/or otherwise connect to the body portion 102 (e.g., to the hooks 130). Such adapters can be included with the breast pump shield 100 and can be disposable, if desired. In another contemplated embodiment, adhesives, elastic connectors, pressure fits, and/or other structures and/or devices can be used to provide universal and/or nearly-universal attachment of the bottle or other receptacle to the breast pump shield 100. It therefore should be understood that the above-described examples are illustrative and therefore should not be construed as being limiting in any way.

FIG. 10 shows the thread attachment mechanism 900 in additional detail. In particular, FIG. 10 is an expanded view of a portion of the thread attachment mechanism 900, as viewed at the view circle C in FIG. 9. It should be understood that this example is illustrative and therefore should not be construed as being limiting in any way.

The thread attachment mechanism 900 can include a body 1002. The body 1002 can be formed by cutting material from the main body portion to create a gap 1004. Thus, the body 1002 can be formed at as a separate piece (relative to the remainder of the body portion 102) and/or can be formed from the body portion 102. It should be understood that these examples are illustrative and therefore should not be construed as being limiting in any way.

In the illustrated embodiment, the body 1002 is formed as a separate piece and joined to the body portion 102 to provide the functionality associated with the thread attachment mechanism 900. With collective reference to FIGS. 9-11, the structure of the thread attachment mechanism 900 will be described in additional detail.

In the illustrated embodiment, the thread attachment mechanism 900 includes a pin insertion structure 1006. A pin, axle, or other structure ("pin") 1008 can be inserted through the pin insertion structure 1006 and held in place by a portion of the body portion 102. Thus, the body 1002 of the thread attachment mechanism 900 can rotate about an axis formed by the pin 1008, e.g., through a center of the pin insertion structure 1006 and/or an aperture formed therein. It should be understood that this example is illustrative and therefore should not be construed as being limiting in any way.

The thread attachment mechanism 900 also can include a thread engagement tooth 1010 and/or two or more thread engagement teeth 1010. The thread engagement tooth 1010 can be configured to engage a thread of a bottle (e.g., a baby bottle). Thus, some embodiments of the thread attachment mechanism 900 can provide a structure that can engage male threads of a bottle instead of including female threads on the inside of the body portion 102. It should be understood that this example is illustrative and therefore should not be construed as being limiting in any way.

In particular, the thread engagement tooth 1010 (and/or combination of two or more thread engagement teeth 1010) can be configured to pass over male threads of a bottle or other container (e.g., by spring loading the body 1002 such that the thread engagement tooth 1010 can move over the threads via rotation of the thread engagement tooth 1010 via rotation of the body 1002 about the axis or pin 1008 as will be appreciated with reference to the FIGURES). After the thread engagement tooth 1010 passes over the threads of the bottle, the body 1002 can rotate back into position and the engagement surface 1012 of the thread engagement tooth 1010 can engage the threads of the bottle or other container, thereby holding the bottle or other container in position to receive milk from the breast pump shield 100 without requiring screwing of the bottle or other container into the body portion 102. It should be understood that this example is illustrative and therefore should not be construed as being limiting in any way.

The body 1002 of the thread attachment mechanism 900 also can include finger grips 1014 and/or a spring 1016, as can be appreciated from the description above. As can be seen in FIGS. 9-10, a ledge 1018 can be formed in the body portion 102 to provide a surface against which the spring 1016 can work, if desired. It should be understood that this example is illustrative and therefore should not be construed as being limiting in any way.

As such, various embodiments of the concepts and technologies described herein can provide a universal attachment (and/or nearly universal attachment) for the breast pump shield 100 for either milk bags and/or bottles. It should be understood that this example is illustrative and therefore should not be construed as being limiting in any way.

Figure 12A:
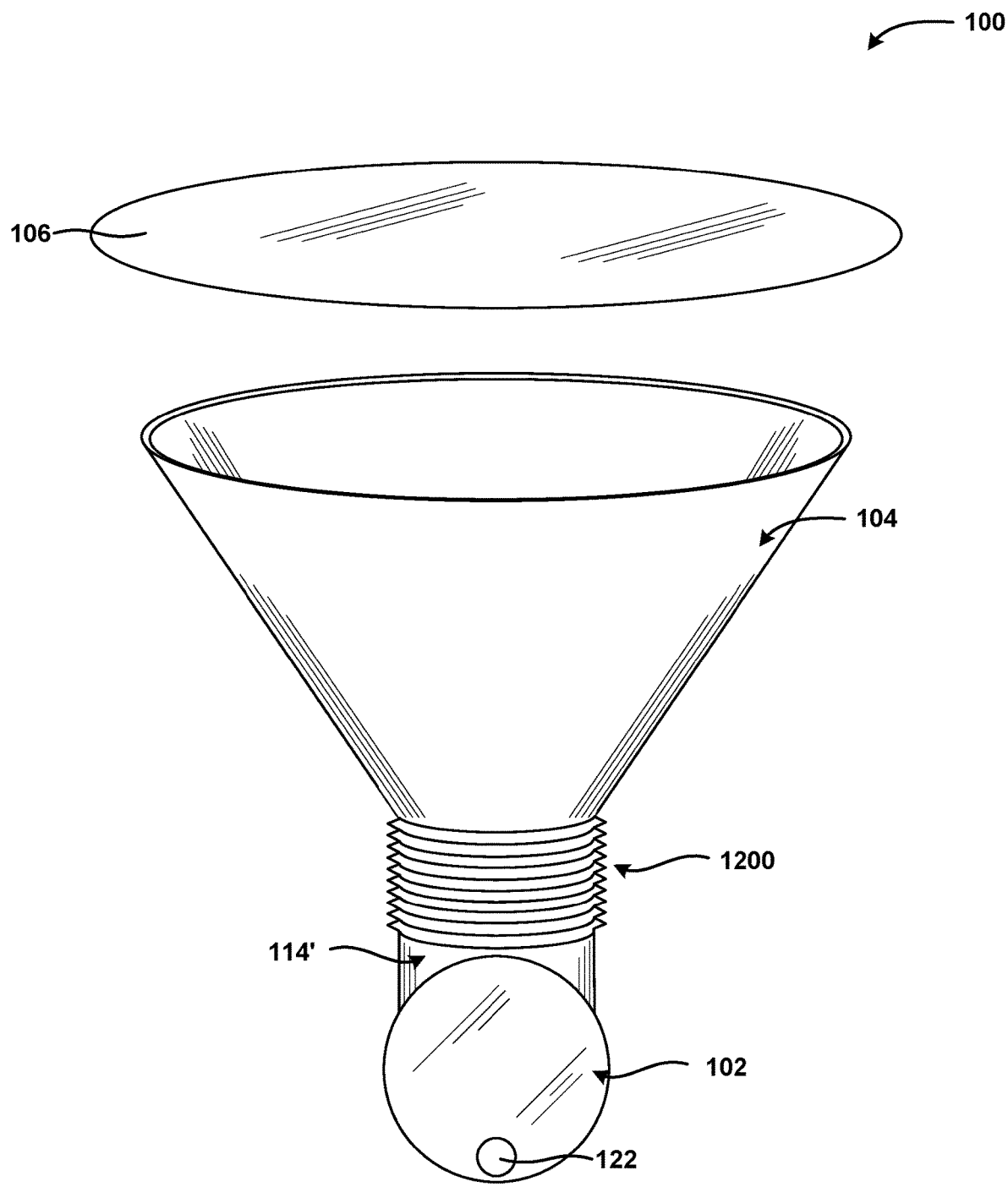
FIGS. 12A-12B are line drawings illustrating top elevation views of a breast pump shield, according to another illustrative embodiment of the concepts and technologies described herein.
Figure 12B:
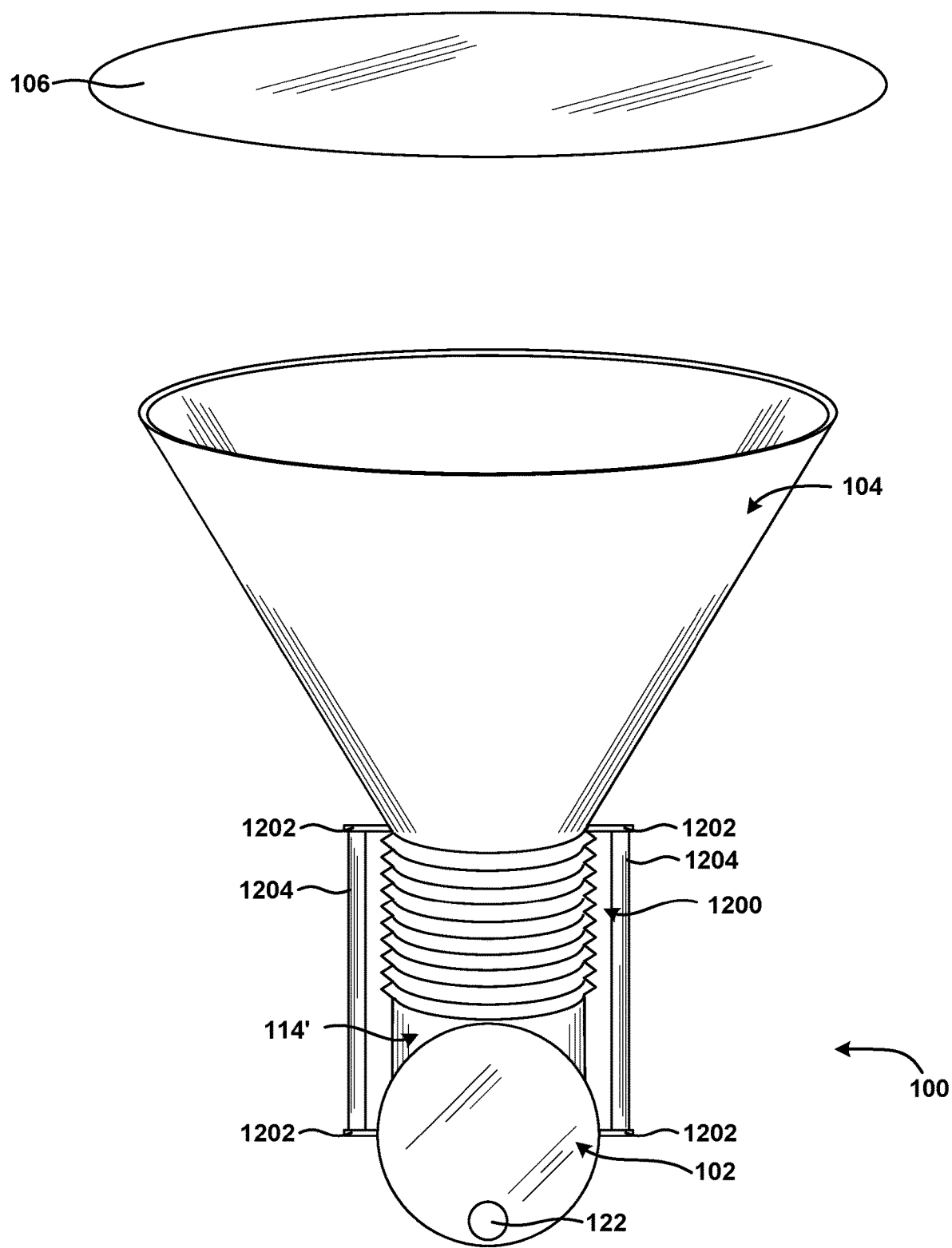

Turning to FIGS. 12A-12B, additional details of the breast pump shield 100 are illustrated and described in detail. In particular, FIGS. 12A-12B are line drawings illustrating top elevation views of a breast pump shield, according to another illustrative embodiment of the concepts and technologies described herein. Because the various components of the breast pump shield 100 can be arranged in various configurations, it should be understood that the views shown in FIGS. 12A-12B could also correspond to side elevation views and/or bottom elevation views instead of, or in addition to, top elevation views.

As shown in FIG. 12A, some embodiments of the breast pump shield 100 can include an expandable and/or collapsible funnel insertion portion 114'. In various embodiments, the expandable and/or collapsible funnel insertion portion 114' can include an expandable and collapsible ridged portion (hereinafter referred to as a "ridged portion") 1200. The ridged portion 1200 can be collapsed or expanded based on desires or needs of a user. In the embodiment shown in FIG. 12A, the ridged portion 1200 of the collapsible funnel insertion portion 114' is illustrated as being collapsed, while in FIG. 12B, ridged portion 1200 of the collapsible funnel insertion portion 114' is illustrated as being expanded. In some embodiments, the funnel portion 104 can be formed as part of (or an extension of) the collapsible funnel insertion portion 114' instead of being formed as two pieces as illustrated and described herein. It should be understood that these examples are illustrative and therefore should not be construed as being limiting in any way.

In some embodiments, the ridged portion 1200 can be included on the breast pump shield 100 to collapse the breast pump shield 100, at least partially, to make the size of the breast pump shield 100 compact. Thus, when the ridged portion 1200 is collapsed, the breast pump shield 100 may consume less space in a diaper bag, glove compartment, purse, or other area for convenience. In some embodiments, the ridged portion 1200 also can be used to protect the lubricant layer. In particular, the ridges of the ridged portion 1200 can be used to hold or retain the lubricant used to provide the lubricant layer at a desired location. It should be understood that this example is illustrative and therefore should not be construed as being limiting in any way.

In some embodiments, an example of which is shown in FIG. 12B, the breast pump shield 100 can include support structures such as the supports 1202 and the support rods 1204. According to various embodiments, the supports 1202 and/or the rods 1204 can be formed from plastics, metals, alloys, thermoplastics, acrylics, epoxies and/or resins, wood, glass, and/or other materials. The support structures can be used to hold the breast pump shield 100 in a configuration at which the ridged portion 1200 is expanded. It can be appreciated that the suction generated by the breast pump (whether manual or electronic) can be sufficient to collapse the ridged portion 1200, which can reduce the realized suction at the nipples of the user. Thus, some embodiments such as the example shown in FIG. 12B include the support structures. In some embodiments, the rods 1204 can be removable and/or reusable. As such, the rods 1204 can be removed, and the ridged portion 1200 can be collapsed, if desired.

Although not visible in the FIGURES, some embodiments of the concepts and technologies described herein include additional supports 1202 and rods 1204. In particular, supports can be located near the beginning of the collapsible funnel insertion portion 114'. Thus, some embodiments of the concepts and technologies described herein can make use of collapsible and/or soft or semi-soft materials for the body portion 102. A collapsible or semi-collapsible body portion 102 can be provided with support by the supports 1202 and rods 1204. It should be understood that these examples are illustrative and therefore should not be construed as being limiting in any way.

According to various embodiments of the concepts and technologies described herein, the breast pump shield 100 is configured to provide a universal or nearly-universal disposable breast pump shield 100 that can be used with various brands of breast pumps. Thus, the breast pump shield 100 can be used by almost any user, regardless of what brand and/or model breast pump the user owns and/or uses. It should be understood that various modifications can be made to the threads, thread attachment mechanisms 900, hooks 130, and/or other structures to realize this goal of providing a universal and/or nearly universal breast pump shield 100.

According to some embodiments of the concepts and technologies described herein, the breast pump shield 100 can be offered in various sizes and/or options. Additionally, or alternatively, the funnel portions 104 can be provided in various sizes and/or models that can provide various options. In some embodiments, for example, the funnel portions 104 can be offered in smooth and/or ribbed configurations, depending upon users' preferences. It should be understood that these examples are illustrative and therefore should not be construed as being limiting in any way.

In some contemplated embodiments, the breast pump shield 100 and/or portions thereof (e.g., the body portion 102, the funnel portion 104, and/or other portions) can be formed from glow in the dark materials. These embodiments can be useful for mothers and/or other users (e.g., healthcare professionals) during the night and/or in other low-light conditions. It should be understood that this example is illustrative and therefore should not be construed as being limiting in any way.

Figure 13:
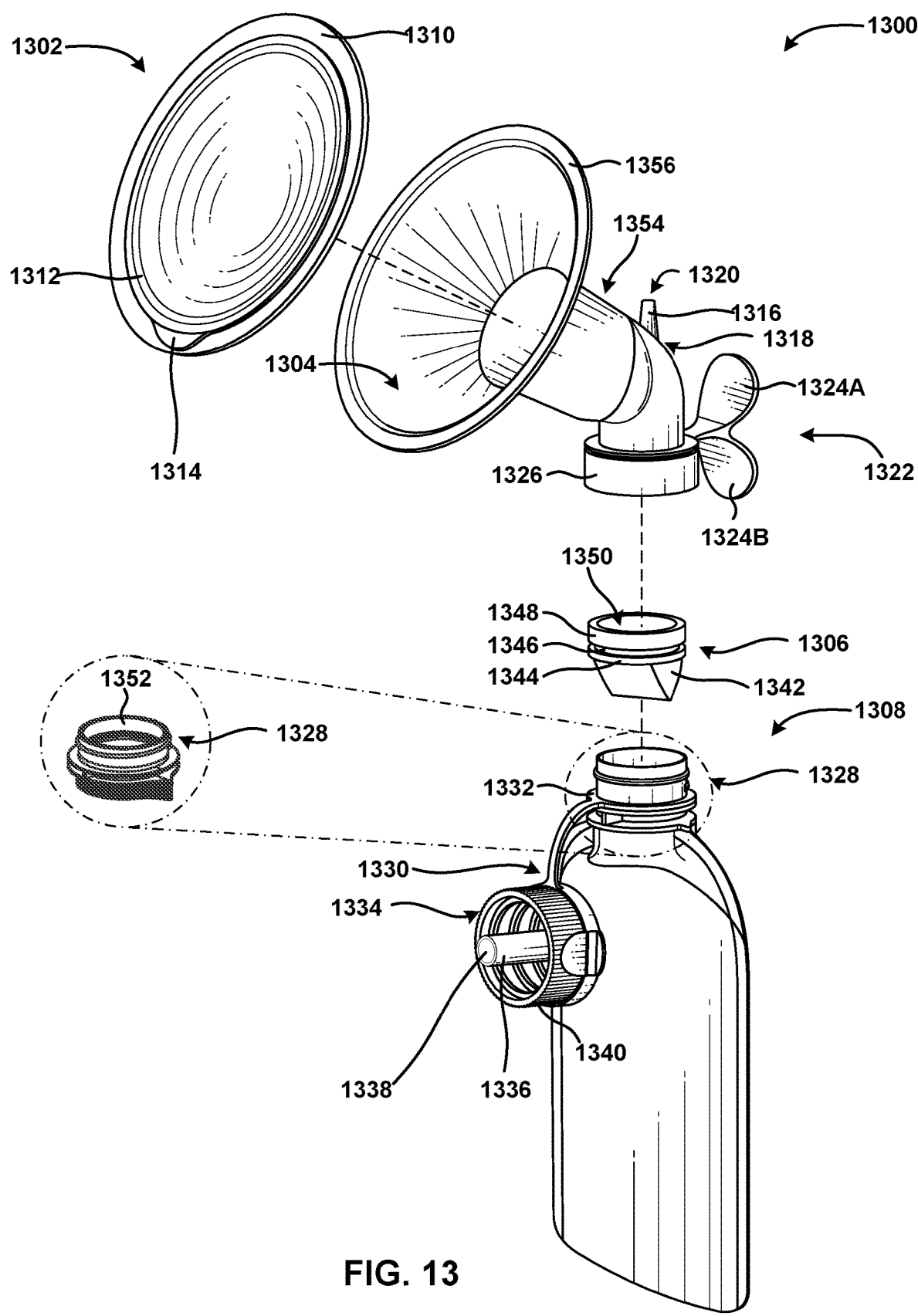
FIG. 13 is an assembly drawing of a breast pump kit, according to an illustrative embodiment of the concepts and technologies described herein.

Turning now to FIG. 13, a breast pump kit 1300 will be described. The breast pump kit 1300 can include one or more components. In some embodiments, the components can include a cover 1302, a breast pump shield 1304, a one-way valve 1306, and a breast pump milk bag 1308. It should be understood that the one-way valve 1306 can be disposed within and/or can be a component of the breast pump milk bag 1308, but is shown in FIG. 13 for ease of description and for clarity. It should be understood that this example is illustrative, and therefore should not be construed as being limiting in any way.

The cover 1302 can include one or more layers. According to various embodiments, the cover 1302 can include one or more of the layers illustrated and described above with reference to FIGS. 1-12B. As such, the cover 1302 can include one or more layers including, but not limited to, a support layer; a wiping layer; a lubricant layer; an adhesive layer, ring, and/or area; other layers; combinations thereof; or the like. It can be appreciated with reference to FIG. 13 that the layers need not be similarly sized with respect to one another. In some embodiments, for example the embodiment shown in FIG. 13, the cover 1302 can include a first layer 1310 having a first diameter and a second layer 1312 having a second diameter. As shown in FIG. 13, the second layer 1312 also can include a grasp area 1314 that can be used to peel the two or more layers apart; to uncover a wipe, lubricant, or other item between the first layer 1310 and the second layer 1312; and/or for other purposes. In some embodiments, the first layer 1310 can correspond to a support layer and the second layer 1312 can correspond to a peelable cover for a lubricant, a wipe, or the like; can correspond to a wipe or other material; combinations thereof; or the like. It should be understood that these examples are illustrative, and therefore should not be construed as being limiting in any way.

As shown in FIG. 13, the breast pump shield 1304 can be formed as a single piece, in some embodiments, or can be formed as multiple pieces. Although illustrated as a single piece in FIG. 13, it can be appreciated that the breast pump shield 1304 can be formed from multiple components such as a funnel portion that can be inserted into a funnel insertion portion etc., as explained above with reference to other embodiments of the concepts and technologies disclosed herein. In the illustrated embodiment, the breast pump shield 1304 can include an inlet projection 1316. As shown in FIG. 13, the inlet projection 1316 can have a tapered cone shape as indicated generally at 1318, namely the outer diameter of the inlet projection 1316 at a first end 1318 of the inlet projection 1316 can have a first diameter that is larger than the outer diameter of the inlet projection 1316 at a second end 1320 of the inlet projection 1316. Thus, the inlet projection 1316 can accommodate tubes or hoses from various breast pumps according to various embodiments.

The breast pump shield 1304 also can include an ergonomic handle 1322. The ergonomic handle 1322 can include one or more finger grasp projections 1324A-B (hereinafter collectively and/or generically referred to as "finger grasp projections 1324"). The finger grasp projections 1324 can be configured to enable a user to grasp the breast pump shield easily and comfortably with one hand. In the illustrated embodiment, which includes two finger grasp projections 1324, the ergonomic handle can be passed through two fingers of the user and the finger grasp projections 1324 can rest against the fingers (e.g., the inner surface of the finger grasp projections 1324 (the surface closes to the inlet projection 1316 in FIG. 13) can contact the finger between the knuckle and the first joint on the side of the hand that is away from the palm). Because additional and/or alternative structures can provide a handle and/or ergonomic handle 1322, it should be understood that this example is illustrative, and therefore should not be construed as being limiting in any way.

The breast pump shield 1304 can include a breast engagement portion. Because the breast engagement portion has already been described above (including the notion of various sizes and configurations, assembly, etc.), this portion of the breast pump shield 1304 will not be further described here. Features and/or structures illustrated and described herein with regard to various embodiments can be combined with one another to create new embodiments not explicitly illustrated in the FIGURES and/or described herein. Thus, for example, the breast pump shield 1304 can include an attachable funnel portion, etc., without departing from the scope of the claims. Other such substitutions and/or variations as illustrated and described herein can be made to various embodiments of the concepts and technologies disclosed herein without departing from the scope of the claims. It should be understood that these examples are illustrative, and therefore should not be construed as being limiting in any way.

The breast pump shield 1304 also can include an engagement portion 1326, which can engage the breast pump milk bag 1308 as noted above. In the illustrated embodiment, the engagement portion 1326 can include threads (not visible in FIG. 13) or other connection mechanisms as illustrated and described herein. Various connection mechanisms as illustrated and described herein with regard to other embodiments of breast pump shields can be used in accordance with the concepts and technologies disclosed herein. As such, the connection mechanisms will not be further described here.

Figure 14A:
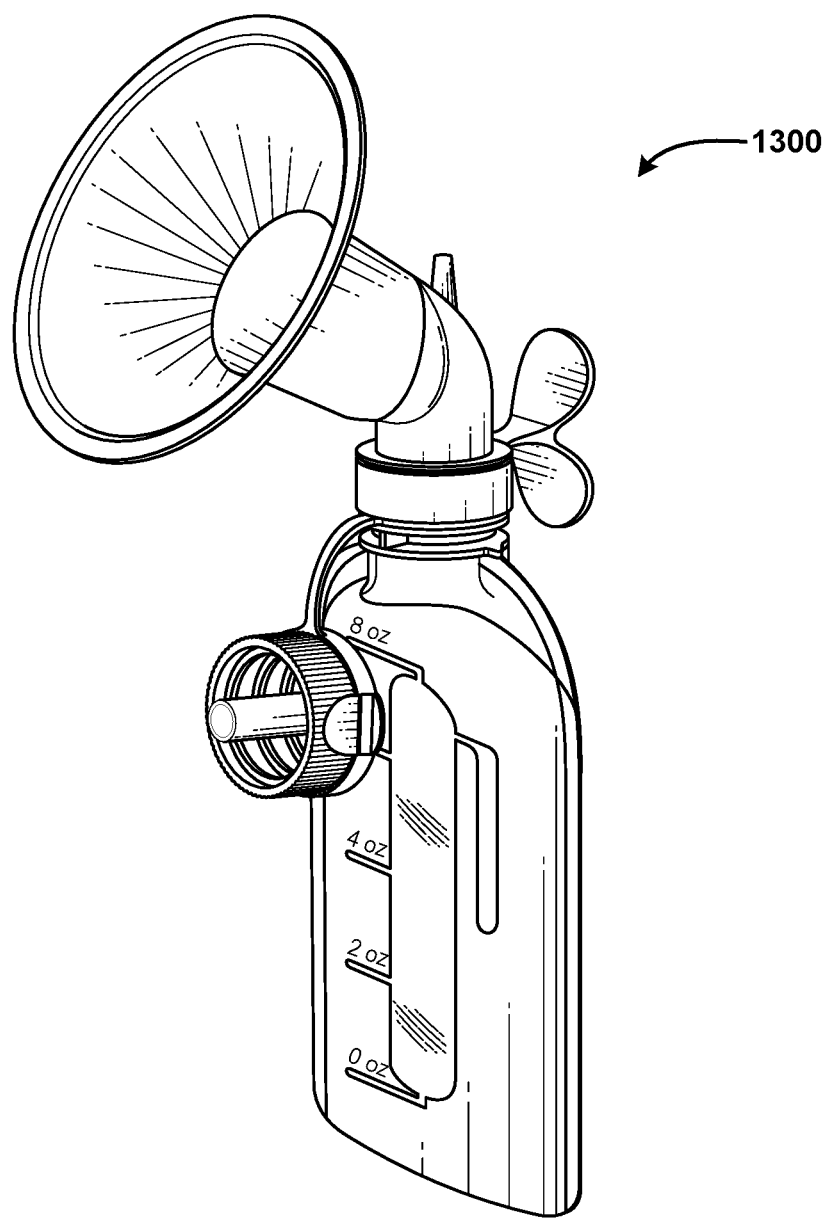
FIGS. 14A-14B are line drawings illustrating perspective views of breast pump kits, according to some illustrative embodiments of the concepts and technologies described herein.
Figure 14B:
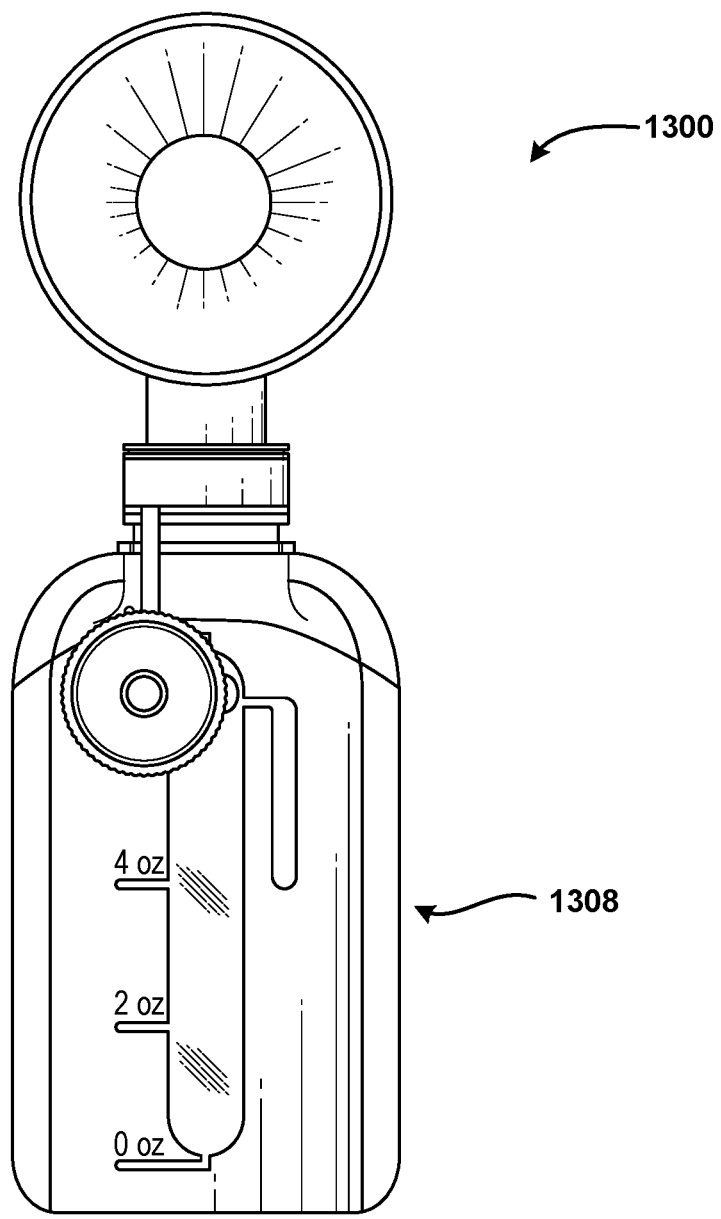

The engagement portion 1326 can engage a bag engagement portion 1328 to hold the breast pump milk bag 1308 in place and/or in an orientation that enables filling of the breast pump milk bag 1308 during lactation. As noted above, the breast pump milk bag 1308 and/or the breast pump shield 1304 can include and/or can engage the one-way valve 1306. Thus, upon assembling the breast pump shield 1304 (with or without the cover 1302) with the one-way valve 1306 and the breast pump milk bag 1308, the breast pump kit 1300 can be ready to use. Two views of the assembled breast pump kit 1300 are shown in FIGS. 14A and 14B. It should be understood that these examples are illustrative, and therefore should not be construed as being limiting in any way.

As can be seen in FIGS. 13-14B, the breast pump kit 1300 can include a cover assembly 1330. It should be understood that the cover assembly 1330 can be joined to the breast pump milk bag 1308, in some embodiments. The cover assembly 1330 can include an attachment ring 1332, which can be used to attach the cover assembly 1330 to the breast pump milk bag 1308. The cover assembly 1330 also can include a cover engagement portion 1334, which can be configured to engage the bag engagement portion 1328. It can be appreciated that the connection mechanism included on the cover engagement portion 1334 (illustrated as threads in FIG. 13) can be substantially similar (in structure) to the connection mechanism formed on the engagement portion 1326 of the breast pump shield 1304. It should be understood that this example is illustrative, and therefore should not be construed as being limiting in any way.

The cover assembly 1330 can also include a valve bypass 1336. The valve bypass 1336 can be configured to enable passage of fluids (e.g., air, liquids, etc.) from the breast pump milk bag 1308 to outside the breast pump milk bag 1308 by bypassing or disabling the one-way valve 1306. Namely, the valve bypass 1336 can be configured to penetrate the one-way valve 1306 and to allow fluids to flow between the breast pump milk bag 1308 and outside the breast pump milk bag 1308 via a passageway 1338 formed in the valve bypass 1336. Via the passageway 1338, fluids can flow (e.g., milk can be poured or forced with pressure through the passage way 1338; air can equalize; etc.). As shown in various FIGURES, the cover engagement portion 1334 can include projections 1340 to provide grip to a user attaching or detaching the cover assembly 1330 from the breast pump milk bag 1308. It should be understood that these examples are illustrative, and therefore should not be construed as being limiting in any way. Additional aspects of the cover assembly 1330 and/or components and/or portions thereof will be illustrated and described in more detail below with reference to the remaining FIGURES.

As shown in FIG. 13, the one-way valve 1306 also can include various structures. In particular, the one-way valve 1306 can include a duckbill valve or other one-way flow mechanism (hereinafter referred to as a "duckbill valve 1342"). The duckbill valve 1342 can have multiple flaps that are joined together by a force to prevent passage of fluids. According to various embodiments of the concepts and technologies disclosed herein, the one-way valve 1306 can be formed from silicone, rubber, or other materials that can be rigid, semi-rigid, or the like. It should be understood that this example is illustrative, and therefore should not be construed as being limiting in any way.

The one-way valve 1306 also can include a first ridge 1344, a trough 1346, and a second ridge 1348. It can be appreciated that an outside diameter of the one-way valve 1306 at the first ridge 1344 can be greater than an outside diameter of the one-way valve 1306 at the trough 1346, though this is not necessarily the case. Similarly, it can be appreciated that an outside diameter of the one-way valve 1306 at the second ridge 1348 can be greater than an outside diameter of the one-way valve 1306 at the trough 1346, though this is not necessarily the case. In some embodiments, the one-way valve 1306 can engage a ridge (not visible) on the inside of the bag engagement portion 1328 to hold the one-way valve 1306 in place. Thus, the one-way valve 1306 can be inserted into the breast pump milk bag 1308 during assembly and can engage the breast pump milk bag 1308 to hold the one-way valve 1306 in place. It should be understood that this example is illustrative, and therefore should not be construed as being limiting in any way.

As can be seen in FIG. 13, the one-way valve 1306 also can include a flow passage 1350 through which fluids can flow from outside the breast pump milk bag 1308 into the breast pump milk bag 1308. Thus, positive pressure or gravity acting on a fluid (e.g., breast milk) can force or urge breast milk through the flow passage 1350, through the duckbill valve 1342, and into the breast pump milk bag 1308. It also can be appreciated with reference to FIG. 14B that the breast pump milk bag 1308 can include designs for aesthetic or functional purposes. For example, the breast pump milk bag 1308 can include measurements, in some embodiments, to enable a user to measure how much milk has been captured in the breast pump milk bag 1308. It should be understood that this example is illustrative, and therefore should not be construed as being limiting in any way.

The above description has referred to the bag engagement portion 1328. In various embodiments, the bag engagement portion 1328 can be formed as a separate piece that can be connected and/or attached to the breast pump milk bag 1308. In some contemplated embodiments, the bag engagement portion 1328 can be formed as a fitment 1352 and/or as a portion of a fitment 1352. In the illustrated embodiment, the bag engagement portion 1328 corresponds to a portion of the fitment 1352. It should be understood that this example is illustrative, and therefore should not be construed as being limiting in any way.

The fitment 1352 can be formed as part of the breast pump milk bag 1308, or formed as a separate piece and joined to the breast pump milk bag 1308. In some contemplated embodiments, the fitment 1352 can be formed from a different material than the material used for the breast pump milk bag 1308 and therefore can be attached or otherwise connected to the breast pump milk bag 1308. In one contemplated embodiment, the fitment 1352 can be formed from acrylonitrile butadiene styrene ("ABS") or other polymers such as thermoplastic polymers or copolymers, or the like. The breast pump milk bag 1308 can be formed with an opening that accepts the fitment 1352, and the fitment 1352 can be located within the opening. In some embodiments, the fitment 1352 can be ultrasonically welded into the breast pump milk bag 1308 to hermetically seal the connections between the fitment 1352 and the breast pump milk bag 1308. It should be understood that this example is illustrative, and therefore should not be construed as being limiting in any way.

According to various embodiments of the concepts and technologies disclosed herein, the components of the breast pump kit 1300 can include various embodiments of the breast pump shield illustrated and described herein including, but not limited to, the breast pump shield 1304 and/or various embodiments of the breast pump shield 100 illustrated and described above. Similarly, the breast pump kit 1300 can include various types of breast milk bags including, but not limited to, the breast pump milk bag 1308 and/or various embodiments of the milk bag 132 as illustrated and described hereinabove. Similarly, the breast pump shield 1304 can be made from various materials including, but not limited, to those listed above with respect to the various embodiments of the breast pump shield 100. In one contemplated embodiment, the breast pump shield 1304 can be formed from polypropylene. In some embodiments, the polypropylene can be translucent, clear, painted, dyed, and/or combinations thereof for aesthetic and/or functional purposes; and the polypropylene also can be smooth, textured, and/or combinations thereof; for aesthetic and/or functional purposes. It should be understood that this example is illustrative, and therefore should not be construed as being limiting in any way.

In some embodiments, the one-way valve 1306 can be formed from silicone or other polymers and/or copolymers. In some embodiments, a thermoplastic elastomer is preferred such as one or more thermoplastic vulcanizates ("TPV"). In some contemplated embodiments, the one-way valve 1306 can be formed from santoprene. In another embodiment, santoprene 20 can be used for the one-way valve 1306. The santoprene can be dyed in some embodiments. It should be understood that these examples are illustrative, and therefore should not be construed as being limiting in any way.

In some embodiments, the cover assembly 1330 can be formed from polypropylene or other polymers, copolymers, or other materials. The components of the cover assembly 1330 can be dimensioned to provide hermitic seals when engaged with one another, as will be more clearly appreciated with reference to FIG. 19. Although not separately described with respect to FIG. 13, it should be understood that the throat portion 1354 of the breast pump shield 1304 and/or the ring 1356 of the breast pump shield 1304 can provide various functions and/or can have various structures and/or features as illustrated and described hereinabove with reference to various embodiments of the breast pump shield 100. It should be understood that this example is illustrative, and therefore should not be construed as being limiting in any way.

Figure 16:
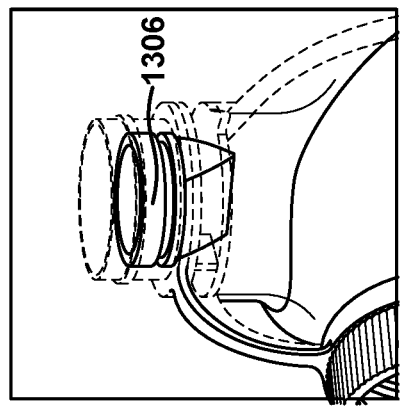
FIG. 16 is a line drawing illustrating a partial perspective view of the breast pump milk bag shown in FIG. 15, according to an example embodiment of the concepts and technologies disclosed herein.
Figure 15:
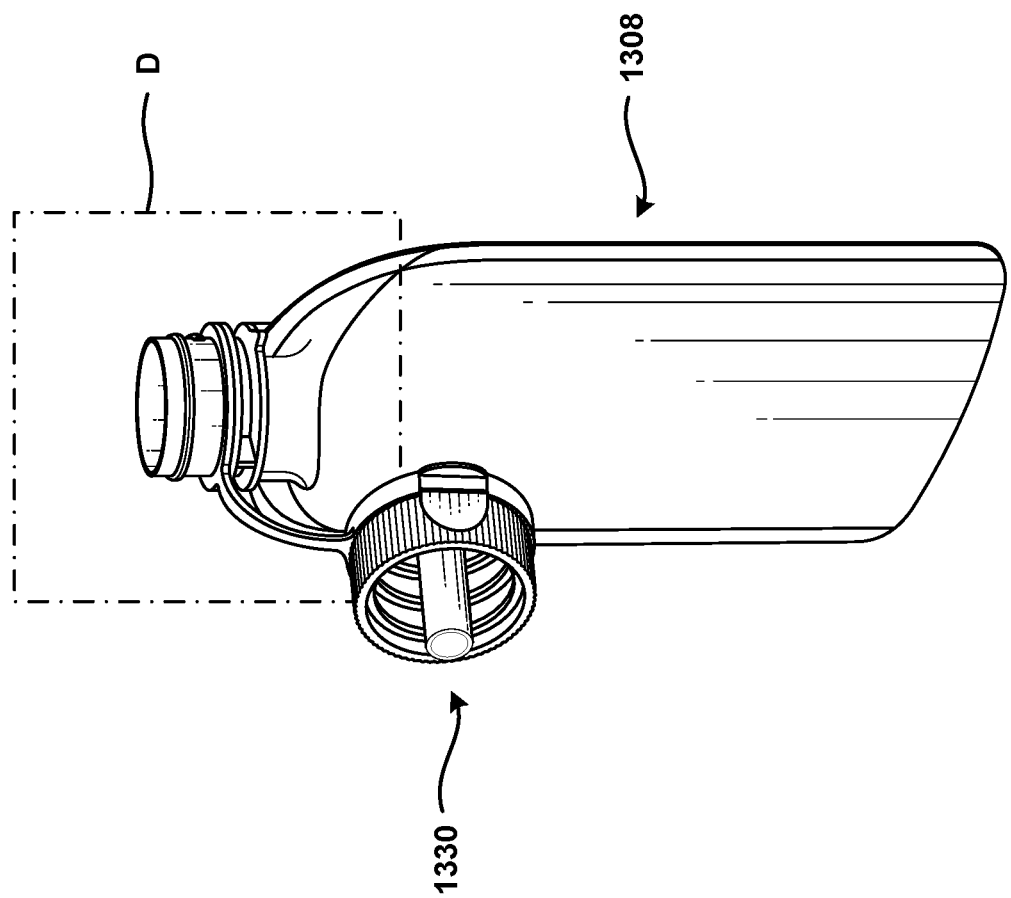
FIG. 15 is a line drawing illustrating a perspective view of a breast pump milk bag, according to an example embodiment of the concepts and technologies disclosed herein.
Figure 17:
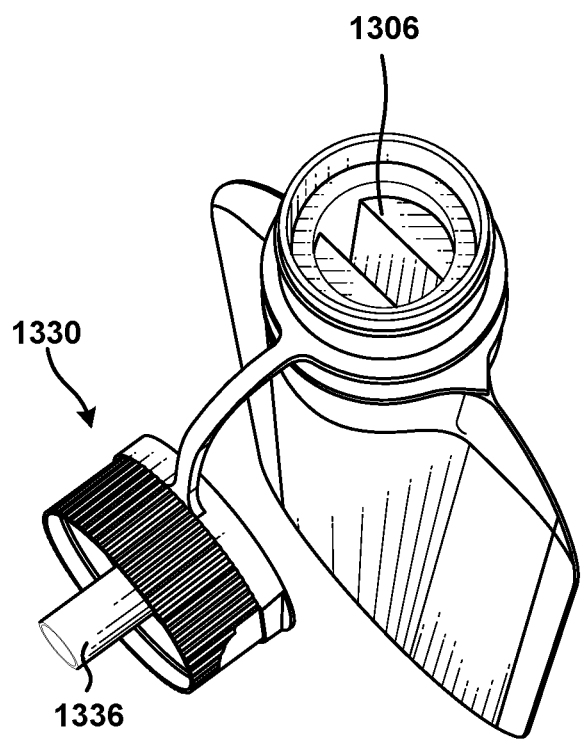
FIG. 17 is a line drawing illustrating another perspective view of the breast pump milk bag shown in FIG. 15, according to an example embodiment of the concepts and technologies disclosed herein.

Turning now to FIGS. 15-16, a portion of the breast pump milk bag 1308 shown in FIG. 15 is shown in partial transparency in FIG. 16. Namely, FIG. 16 illustrates the portion of the breast pump milk bag 1308 as indicated by the view line D in FIG. 15. This FIG. 1s included to show the one-way valve 1306 nested into the breast pump milk bag 1308 as explained above. As shown in FIGS. 15-16, the cover assembly 1330 is not engaged to the breast pump milk bag 1308. As such, fluid in the breast pump milk bag 1308 is sealed and leakage and/or spillage is prevented by way of the one-way valve 1306. Thus, for example, if the breast pump milk bag 1308 contains (e.g., is full or partially full of) milk, the one-way valve 1306 can prevent spillage or leakage of the milk if the breast pump milk bag 1308 is tilted, dropped, squeezed, or the like. A perspective view of the breast pump milk bag 1308 including the one-way valve 1306 is shown in FIG. 17. Also, FIG. 17 shows another view of the cover assembly 1330. It should be understood that these examples are illustrative, and therefore should not be construed as being limiting in any way.

Figure 18:
FIG. 18 is a line drawing illustrating yet another perspective view of a breast pump milk bag, according to an example embodiment of the concepts and technologies disclosed herein.

Turning now to FIG. 18, the breast pump milk bag 1308 is again shown. In FIG. 17, however, the cover assembly 1330 has been connected to the breast pump milk bag 1308 by way of engaging the cover engagement portion 1334 to the bag engagement portion 1328. It can be appreciated from the above description that the one-way valve 1306 can be bypassed in this configuration by way of the valve bypass 1336, which can penetrate the one-way valve 1306 in this configuration. Nonetheless, the breast pump milk bag 1308 can still be sealed by way of the cover assembly 1330. As such, again, fluid in the breast pump milk bag 1308 can be sealed and leakage and/or spillage is prevented by way of the cover assembly 1330. Thus, for example, if the breast pump milk bag 1308 contains (e.g., is full or partially full of) milk, the cover assembly 1330 can prevent spillage or leakage of the milk if the breast pump milk bag 1308 is tilted, dropped, squeezed, or the like. It should be understood that these examples are illustrative, and therefore should not be construed as being limiting in any way.

Figure 20:
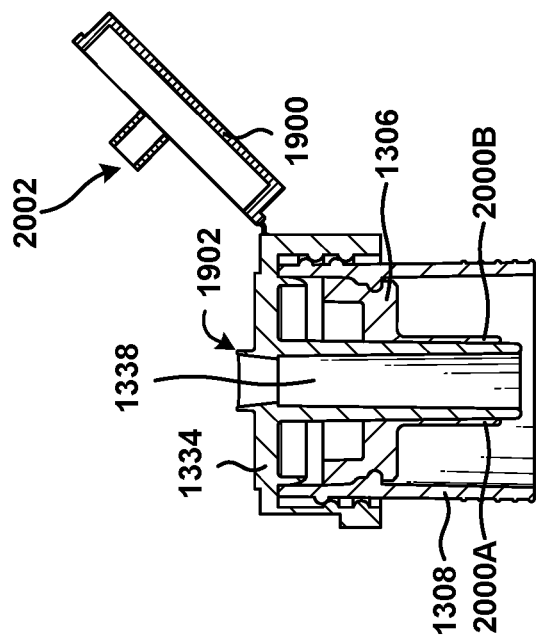
FIG. 20 is a line drawing illustrating a cutaway view of the cover assembly and the breast pump milk bag, according to an example embodiment of the concepts and technologies disclosed herein.
Figure 19:
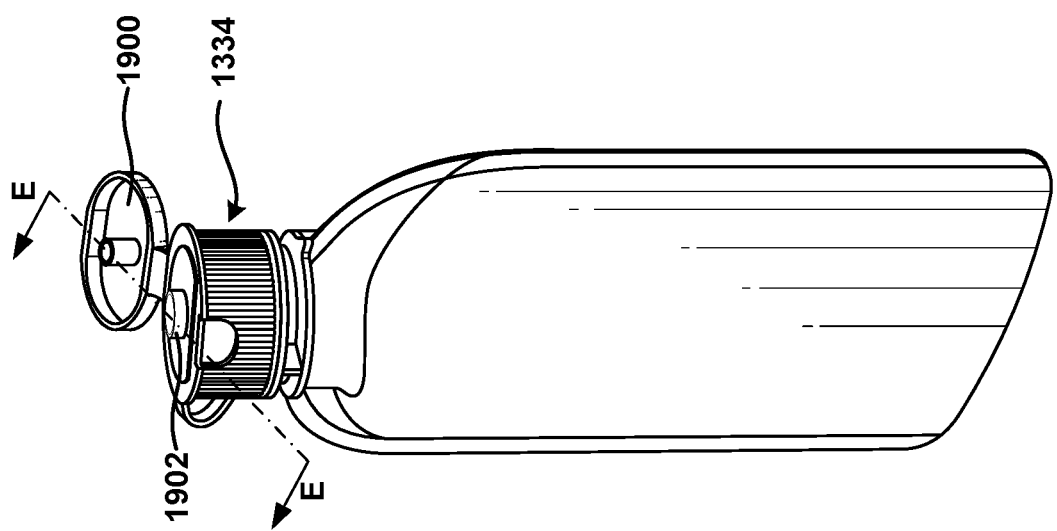
FIG. 19 is a line drawing illustrating still another perspective view of a breast pump milk bag, according to an example embodiment of the concepts and technologies disclosed herein.

Turning now to FIG. 19, the cover assembly 1330 is shown opened. In the view shown in FIG. 19, it can be appreciated that the cover assembly 1330 can be selectively opened to enable flow of the fluids (e.g., milk and air) between the breast pump milk bag 1308 and outside of the breast pump milk bag 1308. In particular, a nozzle cover 1900 of the cover assembly 1330 can be selectively disengaged from the cover engagement portion 1334 to reveal a nozzle 1902. Although not visible in FIG. 19, it can be appreciated that fluids can flow by way of the passageway 1338 formed in the valve bypass 1336 when the nozzle cover 1900 is selective opened. Namely, the passageway 1338 formed in the valve bypass 1336 can extend through the cover engagement portion 1334 and an extension of the passageway 1338 and the valve bypass 1336 can collectively form the nozzle 1902 shown in FIG. 19. A cut-away view of the breast pump milk bag 1308 and the cover assembly 1330 is illustrated in FIG. 20 as viewed along the view line E shown in FIG. 19. As noted above, the nozzle cover 1900 and the nozzle 1902 can be dimensioned such that when the nozzle cover 1900 is closed over the nozzle 1902, the passageway 1338 is hermetically sealed by the respective surfaces of the nozzle cover 1900 and the nozzle 1902. It should be understood that this example is illustrative, and therefore should not be construed as being limiting in any way.

As shown in FIG. 20, the cover engagement portion 1334 of the cover assembly 1330 can engage the breast pump milk bag 1308. The valve bypass 1336 can pass through the one-way valve 1306, thereby pushing flaps 2000A-B (hereinafter collectively and/or generically referred to as "flaps 2000") of the one-way valve 1306 apart to enable bypass of the one-way valve 1306. The passageway 1338 therefore can be seen to pass from within the breast pump milk bag 1308 (and past the one-way valve 1306) to outside of the breast pump milk bag 1308. The nozzle cover 1900 can include a nozzle seal 2002 that can seal the passageway 1338 when the nozzle cover 1900 is closed. It should be understood that this example is illustrative, and therefore should not be construed as being limiting in any way.

Although not shown in the FIGURES, it should be understood that the breast pump milk bag 1308 can be configured to be rolled for packaging, storage, and/or other purposes. In particular, the breast pump milk bag 1308 can be rolled into a tube shape for packaging, storage, and/or other purposes. Similar, as noted above, the ergonomic handle 1322 can be omitted in some embodiments, or substituted with other structures (ergonomically designed or otherwise). Thus, the illustrated structure of the ergonomic handle 1322 should not be construed as being limiting in any way unless this structure is specifically recited in the claims. As noted above in various places, the dimensions of the various components of the breast pump kit 1300 can be varied for various purposes. Also, it is contemplated that the dimensions of the fitment 1352 can be varied to accommodate various breast shields available on the market so that embodiments of the breast pump milk bag 1308 can be sold separately (e.g., not as part of a breast pump kit 1300) and/or can be used with various breast shields including, but not limited to, the various embodiments of the breast pump shields 100, 1304 illustrated and described herein. As such, the illustrated embodiments should be understood as being illustrative and should not be construed as being limiting in any way.

Turning now to FIGS. 21-25, additional aspects of the breast pump milk bag 1308 will be illustrated and described in detail. More particularly, FIGS. 21-25 illustrate several views of the fitment 1352 illustrated and described above with reference to FIG. 13, according to an illustrative embodiment. Various aspects of the fitment 1352 are clear with reference to FIGS. 21-25, but several features are noted for clarity. With reference to FIG. 21, a ridge 2100 is visible. As mentioned above, the trough 1346 of the one-way valve 1306 can be configured to engage the ridge 2100. Thus, the one-way valve 1306 can be inserted in to the bag engagement portion 1328 to engage the ridge 2100 of the fitment 1352. Thus, the breast pump milk bag 1308 can include the fitment 1352 and the inserted one-way valve 1306 as shown illustrated and described with reference to FIG. 17. It should be understood that this example is illustrative, and therefore should not be construed as being limiting in any way.

Turning now to FIG. 22, additional aspects of the breast pump milk bag 1308 and/or the fitment 1352 are shown. With reference to FIG. 22 it can be appreciated that the bag engagement portion 1328 of the fitment 1352 can correspond to a portion of the fitment 1352 that is located outside of the breast pump milk bag 1308, while a second portion 2200 of the fitment 1352 can be located within the breast pump milk bag 1308 after assembly of the breast pump milk bag 1308. As noted above, the fitment 1352 can be inserted into and joined to the breast pump milk bag 1308 using an ultrasonic weld and/or other attachment and/or connection mechanisms such as adhesives, thermoforming, mechanical fasteners, combinations thereof, or the like. It should be understood that the above-noted examples of attachment and/or connection mechanisms are illustrative, and therefore should not be construed as being limiting in any way.

Based on the foregoing, it should be appreciated that embodiments of a breast pump kit have been disclosed herein. Although the subject matter presented herein has been described in conjunction with one or more particular embodiments and implementations, it is to be understood that the embodiments defined in the appended claims are not necessarily limited to the specific structure, configuration, or functionality described herein. Rather, the specific structure, configuration, and functionality are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the embodiments, which is set forth in the following claims.

The invention claimed is:

1. A breast pump kit comprising:
   a breast pump shield comprising a breast engagement portion that is configured to receive least a portion of a human breast, a suction chamber that is located in proximity to the breast engagement portion, and a bag engagement portion comprising an attachment mechanism;
   a breast pump milk bag comprising a bag engagement mechanism that is configured to cooperate with the bag engagement portion to connect the breast pump milk bag to the breast pump shield;
   a one-way valve located inside the breast pump milk bag, wherein the one-way valve comprises two flaps, wherein the breast pump milk bag is configured to receive milk from the suction chamber and via the one-way valve; and
   a cover assembly at the breast pump milk bag, wherein the cover assembly comprises a valve bypass having a passageway, wherein the valve bypass is configured to be selectively inserted through the two flaps of the one-way valve to open the one-way valve, whereby fluid can selectively flow out of the breast pump milk bag through the passageway.

2. The breast pump kit of claim 1, further comprising:
   a cover comprising a support layer, wherein the cover cooperates with the breast pump shield to provide at least part of a hermetic seal for the breast pump shield prior to use.

3. The breast pump kit of claim 2, wherein the cover further comprises a lubricant layer.

4. The breast pump kit of claim 2, wherein the cover further comprises a lubricant layer, wherein the lubricant layer comprises a layer of lubricant, and wherein the breast pump shield is disposable.

5. The breast pump kit of claim 2, wherein the cover further comprises a wiping layer.

6. The breast pump kit of claim 1, wherein the breast pump shield comprises an inlet projection, wherein the inlet projection has a first outer diameter at a first end and a second outer diameter at a second end, and wherein the first outer diameter is larger than the second outer diameter.

7. The breast pump kit of claim 1, wherein the breast pump shield further comprises an ergonomic handle comprising two finger grasp projections.

8. The breast pump kit of claim 1, wherein the cover assembly further comprises:
   a cover engagement portion having a nozzle; and
   a nozzle cover.

9. The breast pump kit of claim 1, wherein the one-way valve comprises a duckbill valve, and wherein the breast pump milk bag is leak resistant and spill resistant.

10. The breast pump kit of claim 1, further comprising a cover that is configured to cooperate with the breast pump shield to provide at least part of a hermetic seal for the breast pump shield prior to use.

11. A breast pump kit comprising:
    a breast pump shield comprising a breast engagement portion that is configured to receive least a portion of a human breast, a suction chamber that is located in proximity to the breast engagement portion, the suction chamber comprising a tapered inlet projection formed thereon and a bag engagement portion comprising an attachment mechanism;
    a breast pump milk bag comprising a bag engagement mechanism that is configured to cooperate with the bag engagement portion to connect the breast pump milk bag to the breast pump shield;
    a one-way valve located inside the breast pump milk bag, wherein the one-way valve comprises two flaps, wherein the breast pump milk bag is configured to receive milk from the suction chamber and via the one-way valve; and
    a cover assembly at the breast pump milk bag, wherein the cover assembly comprises a valve bypass having a passageway, wherein the valve bypass is configured to be selectively inserted through the two flaps of the one-way valve to open the one-way valve, whereby fluid can selectively flow out of the breast pump milk bag through the passageway and through the one-way valve.

12. The breast pump kit of claim 11, further comprising:
    a cover comprising a support layer, wherein the cover cooperates with the breast pump shield to provide at least part of a hermetic seal for the breast pump shield prior to use.

13. The breast pump kit of claim 11, wherein the breast pump shield further comprises an ergonomic handle.

14. The breast pump kit of claim 11, wherein the one-way valve comprises a duckbill valve, and wherein the breast pump milk bag is leak resistant and spill resistant.

15. The breast pump kit of claim 11, wherein the cover assembly comprises:
   a cover engagement portion having a nozzle; and
   a nozzle cover.

16. A breast pump kit comprising:
   a breast pump shield comprising a breast engagement portion that is configured to receive least a portion of a human breast, a suction chamber that is located in proximity to the breast engagement portion, the suction chamber comprising a tapered inlet projection formed thereon and a bag engagement portion comprising an attachment mechanism, wherein the tapered inlet projection has a first outer diameter at a first end and a second outer diameter at a second end, and wherein the first outer diameter is larger than the second outer diameter;
   a breast pump milk bag comprising a bag engagement mechanism that is configured to cooperate with the bag engagement portion to connect the breast pump milk bag to the breast pump shield;
   a one-way valve located inside the breast pump milk bag, wherein the one-way valve comprises two flaps, wherein the breast pump milk bag is configured to receive milk from the suction chamber and via the one-way valve; and
   a cover assembly at the breast pump milk bag, wherein the cover assembly comprises a valve bypass having a passageway, wherein the valve bypass is configured to be selectively inserted through the two flaps of the one-way valve to open the one-way valve, whereby fluid can selectively flow out of the breast pump milk bag through the passageway and through the one-way valve.

17. The breast pump kit of claim 16, further comprising:
   a cover comprising a support layer and a lubricant layer, wherein the cover cooperates with the breast pump shield to provide at least part of a hermetic seal for the breast pump shield prior to use.

18. The breast pump kit of claim 16, wherein the breast pump shield further comprises an ergonomic handle.

19. The breast pump kit of claim 16, wherein the cover assembly comprises:
   a cover engagement portion having a nozzle; and
   a nozzle cover.

20. The breast pump kit of claim 16, wherein the one-way valve comprises a duckbill valve, and wherein the breast pump milk bag is leak resistant and spill resistant.

* * * * *